United States Patent
Kamatani et al.

(10) Patent No.: US 10,403,827 B2
(45) Date of Patent: Sep. 3, 2019

(54) 2,2'-BIBENZO[D]IMIDAZOLIDENE COMPOUND HAVING CONDENSED RINGS AT THE 1-, 1'-, 3- AND 3'-POSITIONS, AND ORGANIC LIGHT-EMITTING ELEMENT, DISPLAY DEVICE, IMAGE INFORMATION PROCESSING APPARATUS, LIGHTING DEVICE, IMAGE FORMING APPARATUS AND EXPOSURE UNIT, EACH CONTAINING THE SAME

(71) Applicant: CANON KABUSHIKI KAISHA, Tokyo (JP)

(72) Inventors: Jun Kamatani, Tokyo (JP); Yosuke Nishide, Kawasaki (JP); Hirokazu Miyashita, Tokyo (JP); Naoki Yamada, Inagi (JP)

(73) Assignee: Canon Kabushiki Kaisha, Tokyo (JP)

( * ) Notice: Subject to any disclaimer, the term of this patent is extended or adjusted under 35 U.S.C. 154(b) by 275 days.

(21) Appl. No.: 15/529,047

(22) PCT Filed: Oct. 20, 2015

(86) PCT No.: PCT/JP2015/005284
§ 371 (c)(1),
(2) Date: May 23, 2017

(87) PCT Pub. No.: WO2016/084303
PCT Pub. Date: Jun. 2, 2016

(65) Prior Publication Data
US 2017/0263870 A1    Sep. 14, 2017

(30) Foreign Application Priority Data
Nov. 27, 2014 (JP) .................. 2014-240622

(51) Int. Cl.
*H01L 51/50* (2006.01)
*H01L 51/00* (2006.01)
(Continued)

(52) U.S. Cl.
CPC ........ *H01L 51/0072* (2013.01); *C07D 235/20* (2013.01); *C07D 401/14* (2013.01);
(Continued)

(58) Field of Classification Search
None
See application file for complete search history.

(56) References Cited

U.S. PATENT DOCUMENTS

2017/0155059 A1* 6/2017 Kamatani ............ C07D 235/20

FOREIGN PATENT DOCUMENTS

| CN | 102439746 A | 5/2012 |
|----|----|----|
| JP | H02238463 A | 9/1990 |

(Continued)

OTHER PUBLICATIONS

Bourson, J., "No. 596—Studies in benzimidazole series III.—Action of bases on 1,3-diphenyl benzimidazolium salts", Bulletin De La Societe Chimique De France, Oct. 4, 1971, pp. 3541-3547, No. 10.
(Continued)

*Primary Examiner* — Gregory D Clark
(74) *Attorney, Agent, or Firm* — Canon U.S.A. Inc., IP Division

(57) ABSTRACT

A stable 2,2'-benzo[d]imidazolidene compound is provided. The 2,2'-benzo[d]imidazolidene compound is expressed by the following General Formula (1). In General Formula (1), $Ar_1$ to $Ar_8$ each represent a substituted or unsubstituted condensed ring. $R_1$ to $R_8$ each represent a hydrogen atom or a substituent.

(Continued)

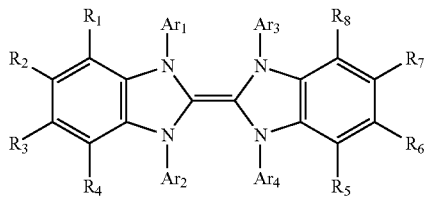

(1)

16 Claims, 5 Drawing Sheets

(51) Int. Cl.
| | |
|---|---|
| C07D 235/20 | (2006.01) |
| C07D 409/14 | (2006.01) |
| C09B 23/10 | (2006.01) |
| C09B 57/00 | (2006.01) |
| C07D 401/14 | (2006.01) |
| G03G 15/04 | (2006.01) |
| H01L 27/32 | (2006.01) |
| H01L 27/12 | (2006.01) |
| H01L 29/786 | (2006.01) |
| H01L 51/52 | (2006.01) |
| H05B 33/08 | (2006.01) |

(52) U.S. Cl.
CPC .......... *C07D 409/14* (2013.01); *C09B 23/102* (2013.01); *C09B 57/00* (2013.01); *G03G 15/04036* (2013.01); *H01L 27/3262* (2013.01); *H01L 51/0058* (2013.01); *H01L 51/0074* (2013.01); *H01L 27/1225* (2013.01); *H01L 29/7869* (2013.01); *H01L 51/5012* (2013.01); *H01L 51/5092* (2013.01); *H01L 51/5206* (2013.01); *H01L 51/529* (2013.01); *H01L 51/5221* (2013.01); *H05B 33/0896* (2013.01)

(56) References Cited

FOREIGN PATENT DOCUMENTS

| | | |
|---|---|---|
| JP | 11-29556 A | 2/1999 |
| JP | 2002-100482 A | 4/2002 |
| JP | 2003-068468 A | 3/2003 |
| JP | 2011-520784 A | 7/2011 |
| JP | 2015-115330 A | 6/2015 |
| JP | 2015-115331 A | 6/2015 |

OTHER PUBLICATIONS

Hahn, Fe., et al., "N,N'-Bis(2,2-dimethylpropyl)benzimidazolin-2-ylidene: A Stable Nucleophilic Carbene Derived from Benzimidazole", Chem. Eur. J., 1999, pp. 1931-1935, vol. 5, No. 6.

Ullah, F., et al., "Annulated N-Heterocyclic Carbenes: 1,3-Ditolylphenanthrenol[9,10-d]imidazol-2-ylidene and Transition Metal Complexes Thereof, Organometallics, Apr. 27, 2009, pp. 2441-2449, vol. 28, No. 8.

Vasudevan, D., et al., "Electroreduction of oxygen in aprotic media", Journal of Electroanalytical Chemistry, 1995, pp. 69-74, vol. 192.

Farman, Ullah, et al., "Annulated N-Heterocyclic Carbenes: 1,3-Ditolylphenanthreno[9,10-dlimidazol-2-ylidene and Transition Metal Complexes Thereof", Organometallics, vol. 28, No. 8, Apr. 27, 2009, pp. 2441-2449.

Mareva, Fevre et al., "Imidazolium Hydrogen Carbonates versus Imidazolium Carboxylates as Organic Precatalysts for N-Heterocyclic Carbene Catalyzed Reactions", Journal of Organic Chemistry, Oct. 23, 2012, vol. 77, No. 22, pp. 10135-10144.

* cited by examiner

2,2'-BIBENZO[D]IMIDAZOLIDENE COMPOUND HAVING CONDENSED RINGS AT THE 1-, 1'-, 3- AND 3'-POSITIONS, AND ORGANIC LIGHT-EMITTING ELEMENT, DISPLAY DEVICE, IMAGE INFORMATION PROCESSING APPARATUS, LIGHTING DEVICE, IMAGE FORMING APPARATUS AND EXPOSURE UNIT, EACH CONTAINING THE SAME

CROSS-REFERENCE TO RELATED APPLICATIONS

This application is a National Stage filing of International Application No. PCT/JP2015/005284 filed Oct. 20, 2015, which claims the benefit of Japanese Patent Application No. 2014-240622, filed Nov. 27, 2014, the disclosures of each of which are hereby incorporated by reference herein in their entirety.

TECHNICAL FIELD

The present invention relates to a 2,2'-bibenzo[d]imidazolidene compound having condensed rings at the 1-, 1'-, 3- and 3'-positions, and an organic light-emitting element, a display device, an image information processing apparatus, a lighting device, an image forming apparatus and exposure unit, each containing the compound.

BACKGROUND ART

An organic light-emitting element includes an anode and a cathode, and an organic compound layer between the anode and the cathode. The organic light-emitting element emits light by recombination of holes injected from the anode and electrons injected from the cathode in a luminescent layer that is a type of the organic compound layer. Recent significant advances in development of organic light-emitting elements have been achieving thin, lightweight light-emitting devices that can emit a variety of emission wavelengths and respond rapidly at a low driving voltage.

In order to reduce the driving voltage of an organic light-emitting element, it is effective to improve the electron injectability of the organic light-emitting element. PTLs 1 and 2 each disclose a technique using a metal for improving the electron injectability.

NPLs 1, 2 and 3 disclose synthesizing processes of compounds expressed by the following General Formulas 1-A, 1-B and 1-C. Unfortunately, these compounds are unstable and easily oxidized in the air. In addition, these compounds have not been described as compounds used in organic electronic elements.

[Chem. 1]

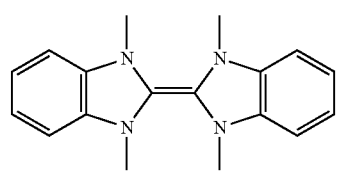

1-A

[Chem. 2]

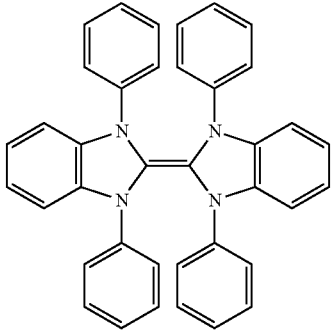

1-B

[Chem. 3]

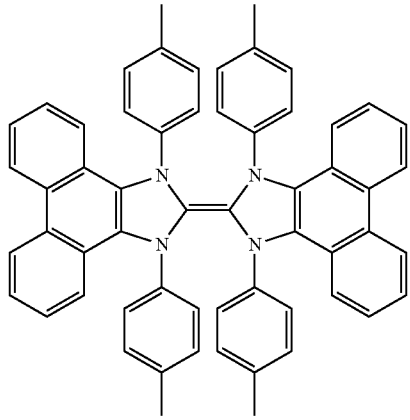

1-C

CITATION LIST

Patent Literature

PTL 1: Japanese Patent Laid-Open No. 2003-068468
PTL 2: Japanese Patent Laid-Open No, 2002-100482

Non Patent Literature

NPL 1: F. Ekkehardt Hahn, N,N'-Bis(2,2-dimethylpropyl)benzimidazolin-2-ylidene: A Stable Nucleophilic Carbene Derived from Benzimidazole", Chemistry-A European Journal (1999), 5, (6), 19311935

NPL 2: Jean Bourson, "Benzimidazoles. III. Action of bases on 1,3-diphenylbenzimidazolium salts", Bulletin de la Societe Chimique de France (1971), (10), 3541-7

NPL 3: Farman Ullah, "Annulated N-Heterocyclic Carbenes: 1,3-Ditolylphenanthreno[9,10-d]imidazol-2-ylidene and Transition Metal Complexes Thereof", Organometallics (2009), 28(8), 2441-2449

NPL 4: D. Vasudevan, "Electroreduction of oxygen in aprotic media", Journal of Electroanalytical Chemistry 192, (1995), 69-74

The electron injection layer of the organic light-emitting elements disclosed in PTLs 1 and 2 contains a compound containing a metallic element. Although such an electron injection layer is advantageous in terms of electron injection property, it is reactive with water and is accordingly likely to reduce the lifetime of the element.

The compounds disclosed in NPLs 1 to 3 are unstable to oxidation in the air. If any one of these compounds is used in an organic electronic element, such as an organic light-emitting element, the element is degraded in terms of stability and lifetime.

SUMMARY OF INVENTION

The present invention provides an organic compound that is stable to oxidation in the air. According to an aspect of the present invention, there is provided a 2,2'-bibenzo[d]imidazolid.ene compound expressed by the following General Formula (1).

[Chem. 4]

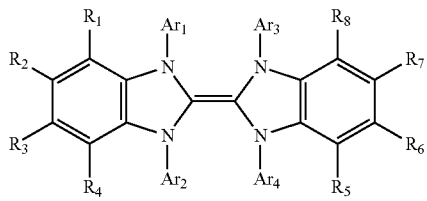

(1)

In General Formula (1), $Ar_1$ to $Ar_4$ each represent a substituted or unsubstituted condensed ring. $R_1$ to $R_8$ each represent a hydrogen atom or a substituent. The substituent is selected from the group consisting of halogen atoms, alkyl groups having a carbon number in the range of 1 to 8, and substituted or unsubstituted aromatic hydrocarbon groups.

Further features of the present invention will become apparent from the following description of exemplary erribodiments with reference to the attached drawings.

DESCRIPTION OF EMBODIMENTS

Figure 1:
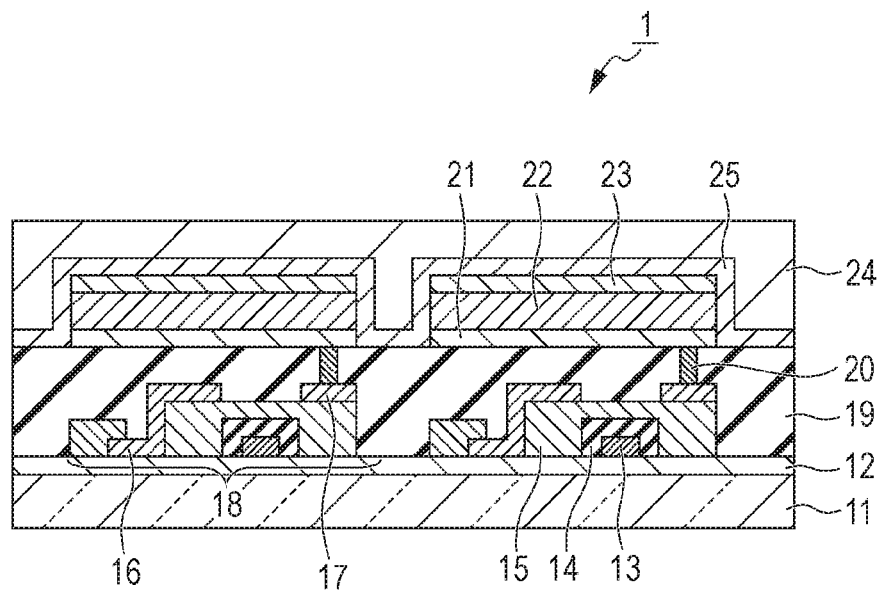
FIG. 1 is a schematic sectional view of a display device including organic light-emitting elements of an embodiment of the present invention and active elements connected to the corresponding organic light-emitting elements.

The present invention provides a 2,2'-bibenzo[d]imidazolidene compound expressed by the following General Formula (1). This compound, which has condensed rings at the 1-, 1'-, 3- and 3'-positions, is less reactive with oxygen or water in the air and can therefore exist stably.

In the following description, the 2,2'-bibenzo[d]imidazolidene compound having condensed rings at the 1-, 1'-, 3- and 3'-positions may be referred to as the present organic compound.

In the description herein, the structure in General Formula (1) in winch all of $Ar_1$ to $Ar_4$ and $R_1$ to $R_8$ are each a hydrogen atom is referred to as the 1,1!,3,3'-tetrahydro-2, 2'-bibenzo[d]imidazolidene skeleton.

The present organic compound is expressed by the following General Formula (I).

[Chem. 5]

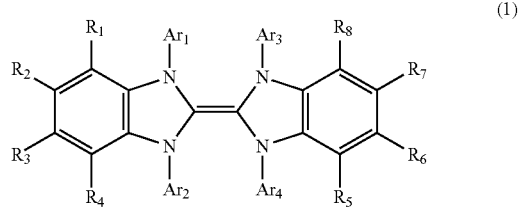

(1)

In General Formula (1), $Ar_1$ to $Ar_4$ each represent a substituted or unsubstituted condensed ring. $R_1$ to $R_8$ each represent a hydrogen atom or a substituent. The substituent is selected from the group consisting of halogen atoms, alkyl groups having a carbon number in the range of 1 to 8, and substituted or unsubstituted aromatic hydrocarbon groups.

In each of the condensed rings, the atom adjacent to the atom bound to the 1,1',3,3'-tetrahydro-2,2'-bibenzo[d]imidazalidene skeleton is desirably not involved in forming the ring.

Desirably, $Ar_1$ and $Ar_2$ are the same substituent, and $Ar_3$ and $Ar_4$ are the same substituent.

The condensed rings represented by $Ar_1$ to $Ar_4$ include naphthyl, indenyl, phenanthrenyl, anthracenyl, pyrenyl, fluorenyl, quinolinyl, isoquinolinyl, aza-phenanthrenyl, phenanthronyl, benzothienyl, dibenzothienyl, benzofuranvl, and dibenzofuranyl.

Among these condensed rings, naphthyl, indenyl, phenanthrenyl, anthracenyl, pyrenyl and fluorenyl are hydrocarbons consisting entirely of hydrogen and carbon.

On the other hand, quinolinyl, isoquinolinyl, azaphenanthrenyl, phenanthronyl, benzothienyl, dibenzothienyl, benz, ofuranyl and dibenzofuranyl are condensed rings each containing a heteroatom. Advantageously, the condensed rings are hydrocarbons.

Each of the condensed rings may have a substituent. The substituent is selected from the group consisting of alkyl groups having a carbon number in the range of 1 to 4; aromatic hydrocarbon groups, such as phenyl, naphthyl, phenanthryl, and fluorenyl; and halogen atoms, such as fluorine, chlorine, bromine, and iodine. if the substituent is a halogen atom, fluorine is advantageous.

The alkyl groups having a carbon number in the range of 1 to 4 include methyl, ethyl, n-propyl, isopropyl, n-butyl, isobutyl, sec-butyl, and tert-butyl.

The halogen atoms represented by $R_1$ to $R_8$ include fluorine, chlorine, bromine, and iodine. Fluorine is advantageous.

Examples of the alkyl groups represented by $R_1$ to $R_8$ having a carbon number in the range of 1 to 8 include methyl, ethyl, n-propyl, isopropyl, n-butyl, isobutyl, sec-butyl, tert-butyl, n-pentyl, n-hexyl, and n-octyl.

Aromatic hydrocarbon groups represented by $R_1$ to $R_8$ include phenyl, naphthyl, phenanthryl, and fluorenyl. Phenyl is advantageous. Each of the aromatic hydrocarbon groups may have a substituent. In this instance, the substituent is selected from the group consisting of alkyl groups having a carbon number in the range of 1 to 4; aromatic hydrocarbon groups, such as phenyl, naphthyl, phenanthryl, and fluorenyl; and halogen atoms, such as fluorine, chlorine, bromine, and iodine. If the substituent is a halogen atom, fluorine is advantageous.

Properties of the Present Organic Compound

The organic compound according to an embodiment of the present invention has condensed rings at the 1-, 1'-, 3- and 3'-positions of the 1,1',3,3'-tetrahydro-2,2'-bibenzo[d] imidazolidene skeleton. By providing the active nitrogen atoms with bulky substituents or condensed rings, the stability of the 1,1',3,3'-tetrahvdro-2,2'-bibenzo[d]imidazolidene skeleton, which is generally unstable and has a low oxidation potential, can be improved.

In addition, the 1,1',3,3'-tetrahydro-2,2'-bibenzo[d]imidazolidene skeleton has a high electron injectability.

The present 1,1',3,3'-tetrahydro-2,2'-bibenzo[d]imidazolidene compound having these two properties is less reactive with oxygen and water in the air and thus exhibits both a high electron injectability and a high stability.

Although organic compounds containing a metallic element exhibit a high electron injectability, metal-free organic compounds are advantageous as the organic compound used in organic electronic elements. The advantage of using a metal-free organic compound in the organic electronic element is that it has a low solubility in water. Know alkali metal-containing compounds, such as lithium fluoride and quinolinol lithium complexes, are soluble in water. If an organic compound containing a metallic element is used in an organic electronic element, carriers can be efficiently injected from an electrode, whereas the compound is likely to be ionized by external moisture or the like. This is a cause of instability of the element.

Accordingly, the use of a metal-free organic compound enables a stable element to be provided.

The organic compound used as the electron injection material desirably has a shallow HOMO (highest occupied molecular orbital) level close to the energy level of the cathode. The term "shallow HOMO level" mentioned herein refers to a low absolute value of the HOMO level and implies that it is closer to the vacuum level. A shallow HOMO level is substantially synonymous with a low first oxidation potential in cyclic voltammetry (CV).

The use of a compound having a shallow HOMO level reduces the energy barrier of electrons to be injected from the cathode to an electron conduction band. From the view point of functioning as an electron injection material, the organic compound desirably has a relatively low first oxidation potential. For example, the first oxidation potential is 0.00 V or less (vs. Fc/Fc$^+$), such as −0.70 V or less (vs. Fc/Fc$^+$). The expression "vs. Fc/Fc$^+$" represents that the first oxidation potential is a value relative to the oxidation-reduction potential of ferrocene.

In an organic light-emitting element including an electron injection layer containing a compound having a shallower HOMO level, that is, having a lower first oxidation potential, electrons can more efficiently injected from the cathode to the electron injection layer.

Organic compounds having a first oxidation potential higher than the oxidation-reduction potential of oxygen are stable to oxygen. Hence, it is advantageous that the present organic compound has a higher first oxidation potential than the oxidation-reduction potential of oxygen. The oxidation-reduction potential ($O_2/O_2^-$) of oxygen is −1.22 V (vs. Fc/Fc$^+$) in DMF (dimethylformamide) NPL 4).

Hence, the first oxidation potential of the organic compound in DMF is desirably in the range of −1.20 V to 0.00 V (vs. Fc/Fc$^+$), and more desirably in the range of −1.20 V to −0.70 V (vs. Fc/Fc$^+$). When the first oxidation potential is within such a range, the organic compound is stable to oxygen and superior in electron injectability.

Oxidation potential can be measured by cyclic voltammetry (CV). More specifically, oxidation potential can be estimated from the peak of oxidation current in a CV curve.

Figure 2:
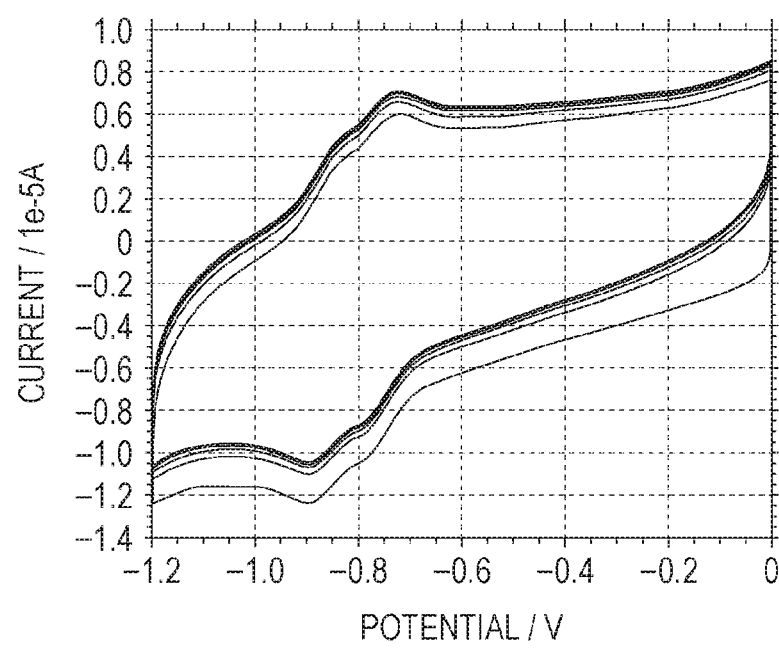
FIG. 2 is a cyclic voltammogram of an organic compound according to an embodiment of the present invention.

FIG. 2 is a cyclic voltammogram of Exemplified Compound A1, which is an organic compound of the present invention.

Exemplified Compound A1 exhibits a reversible oxidation-reduction reaction as shown in FIG. 2 and is thus stable to oxidation and reduction. The oxidation-reduction potential estimated from the peak of oxidation potential is −0.75 V, which is within the range of −1.20 V to 0.00 V.

Since Exemplified Compound A1 has a high oxidation potential, it can act as a donor, and can form a charge transfer complex by being mixed with a compound capable of acting as an accepter. By using this charge transfer complex in the organic compound layer in contact with an electrode in an organic light-emitting element, carriers can be easily injected from the electrode.

On the other hand, Comparative Compounds 3 and 4 did not exhibit an oxidation potential peak of about −1.0 V when measured after being allowed to stand in the air. This suggests that the intrinsic property of these compounds has been lost by oxidation. Comparative Compound 3 has the same structure as Compound 1-A cited as the Background Art, and Comparative Compound 4 has the same structure as Compound. 1-B.

Stabilities to water of the present organic compound and Comparative Examples were examined to estimate the reactivity of these compounds with water in the air. Powders of alkali metal-containing Comparative Compounds 1 and 2, Comparative Compounds 3 and 4, and Exemplified Compounds 1 and 2 according to the present invention were allowed to stand in a high-humidity environment of 95% for 1 hour, and the changes thereof were visually compared. The results are shown in Table 1.

TABLE 1

| | | Reactivity |
|---|---|---|
| Organic Compound 1 of the invention | | Not changed |

TABLE 1-continued

| | | Reactivity |
|---|---|---|
| Organic Compound 2 of the invention | [structure] | Not changed |
| Comparative Compound 1 | LiF | Deliquesced slightly |
| Comparative Compound 2 | CsF | Deliquesced |
| Comparative Compound 3 | [structure] | Turned red |
| Comparative Compound 4 | [structure] | Deliquesced and turned black |

Table 1 shows that Comparative Examples 1 and 2 being alkali metal salts, Comparative Compound 3 containing nitrogen atoms each having a phenyl group, and Comparative Compound 4 containing nitrogen atoms each having an alkyl group deliquesced or oxidized.

In comparison between Comparative Compounds 3 and 4, Comparative Compound 4, in which the nitrogen atoms each have a methyl group, oxidized faster than Comparative Compound 3 and turned black while being deliquescing. This is probably because the substituents of Comparative Compound 4 are methyl groups having a small excluded volume.

On the other hand, the organic compounds according to the present invention did not exhibit changes, such as deliquescence or oxidation, and were stable.

The present organic compound has an electron injectability sufficient as the electron injection material and does not oxidize easily in the air.

The present organic compound has a stability improved by substituting bulky groups at unstable sites of the 1,1',3,3'-tetrahydro-2,2'-bibenzo[d]imidazolidene skeleton.

First, the electron density of each site of the 1,1',3,3'-tetrahydro-2,2'-bibenzo[d]imidazolidene skeleton was estimated by a molecular orbital calculation. The calculation was performed as below. For calculation for the molecular structures in the electronic ground state and electrically excited state, a commercially available electronic state calculation software program Gaussian 03 Revision D. 01 was used. In this operation, Density Functional Theory was adopted as quantum chemical calculation, and B3LYP was used for the functional. The basis function was 6-31G(d).

As shown in Chemical Structural Formula (3), the nitrogen atoms, which are considered to be active, had a large negative charge. Sites of the chemical structure symmetrical each other have the same value.

[Chem. 6]

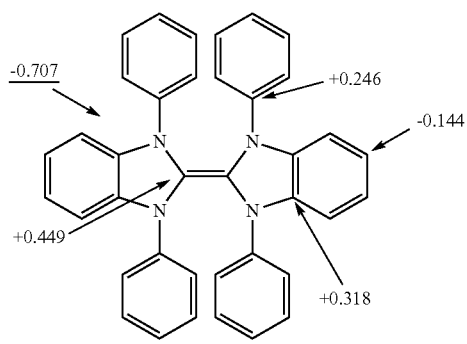

(3)

These results suggest that the 1-, 1'-, 3- and 3'-positions having the largest negative charge, and the 5-, 5'-, 6- and 6'-positions have the second largest. These are probably the cause of instability.

The reason why Comparative Compounds 3 and 4 are unstable in the air is probably that it is insufficient to merely provide methyl or phenyl groups at the 1-, 1'-, 3- and 3'-positions having such a large negative charge.

Accordingly, the present organic compound is provided with condensed rings as substituents, thereby being made stable in the air.

The compound substituted with 2-naphthalene at the 1-, 1'-, 3- and 3'-positions, expressed by the following structural formula (4), that is, 1,1',3,3'-tetra(naphthalene-2-yl)-2,2'-bibenzo[d]imidazolidene, is stable in the air in practice.

The present compound thus substituted with bulky groups is stable in spite of having a low oxidation potential. Such a structure enables a compound having an oxidation potential of less than −0.9 V to be stable in the air.

In the organic compound of the present invention, advantageously, the atoms adjacent to the atoms bound to the nitrogens of the 1,1',3,3'-tetrahydro-2,2'-bibenzo[d]imidazolidene skeleton each have a hydrogen atom. Such an organic compound is more stable. For example, in the case where the condensed rings are naphthyl, the compound expressed by structural formula (4) is more stable than the compound expressed by structural formula (5). In other words, 2-naphthyl is more advantageous than 1-naphthyl.

[Chem. 7]

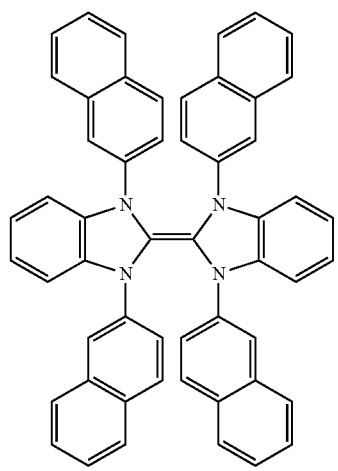 [SMILES: c1ccc2c(c1)N(c1ccc3ccccc3c1)C(=C1N(c3ccc4ccccc4c3)c3ccccc3N1c1ccc3ccccc3c1)N2c1ccc2ccccc2c1]

(4)

[Chem. 8]

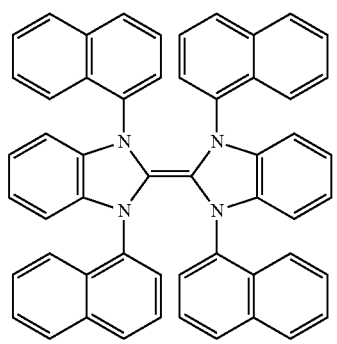

(5)

This is probably because condensed rings bound in a 1-yl form as in the case of structural formula [5] are so bulky that the steric repulsion between the substituents at the 1- and 1'-positions and between the substituents at the 3- and 3'-positions is increased. Accordingly, by using condensed rings in a 2-yl form for substitution, the condensed rings are bound at the 2- and 2'-positions thereof so that the resulting compound bulkily has substituents at the 1-, 1'-, 3- and 3'-positions most effectively The present organic compound is therefore stable in the air.

By using a 2,2'-bibenzo[d]imidazolidene compound having condensed rings at the 1-, 1'-, 3- and 3'-positions having a low oxidation potential in the electron injection layer, the organic element can be more stable than the case of using an alkali metal salt or an alkali metal-containing compound.

It can be checked by subjecting the organic compound layer to TOF-SIMS (Time-of-Flight Secondary Ion Mass Spectrometry) or the like whether or not an organic light-emitting element contains the present organic compound. Alternatively, the organic compound extracted from the organic light-emitting element may he measured with IR or UV or by NMR.

[Exemplary 2,2'-bibenzo[d]imidazolidene Compounds having Condensed Ring Structures at the 1-, 1'-, 3- and 3'-Positions]

There will be shown exemplary 2,2'-bibenzo[d]imidazolidene compounds having condensed ring structures at the 1-, 1'-, 3- and 3'-positions.

[Chem. 9]

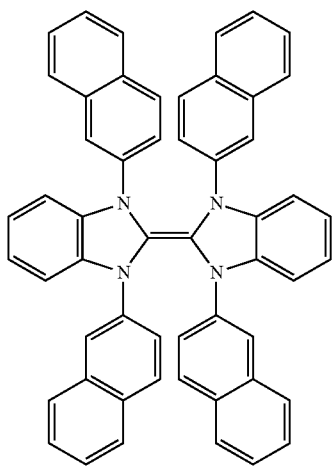

A1

11
-continued
A2
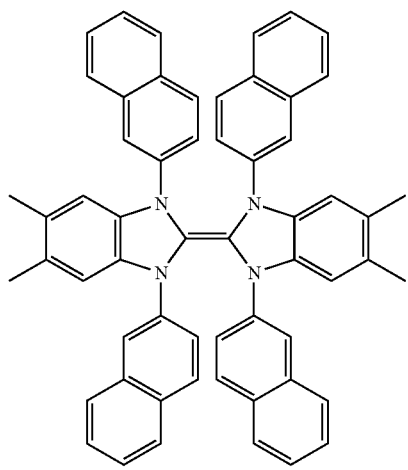
A3
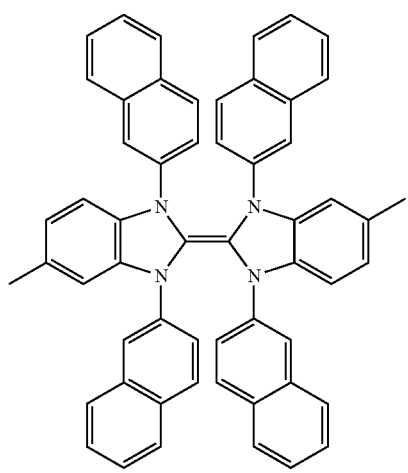
A4
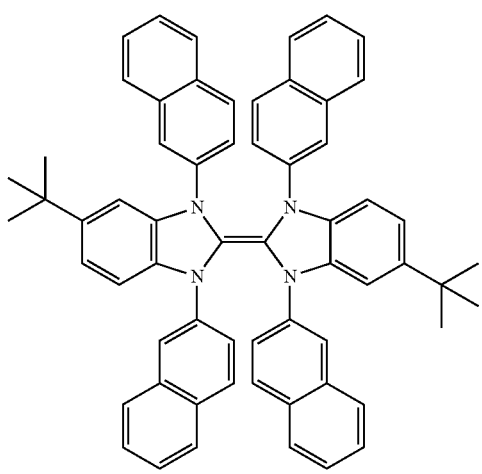
12
-continued
A5
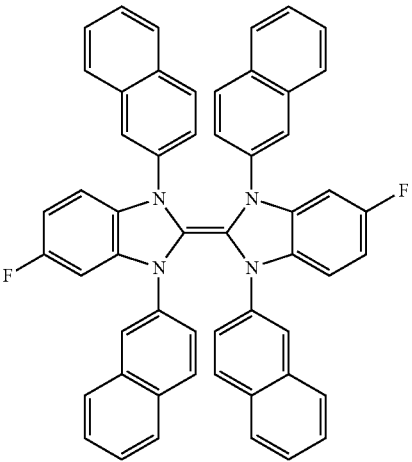
A6
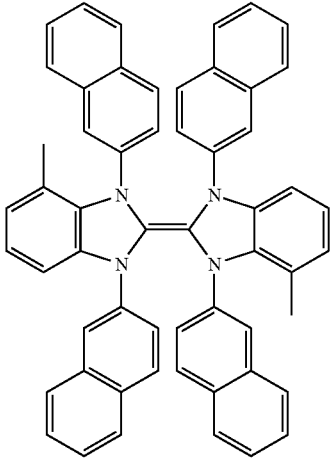
A7
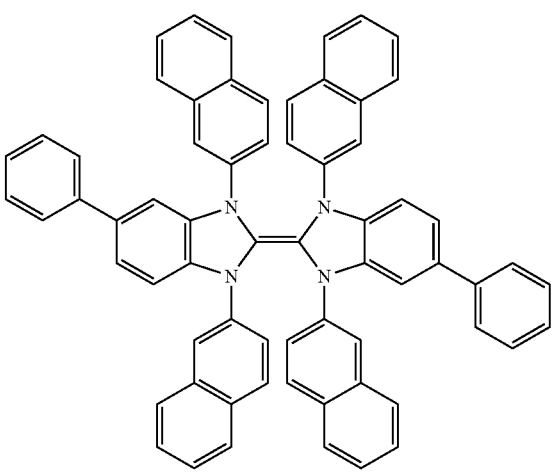

A8
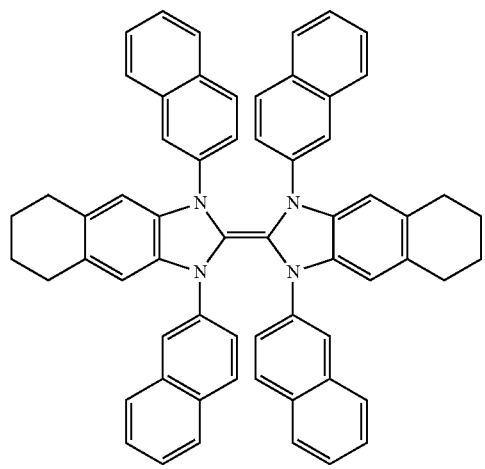
A9
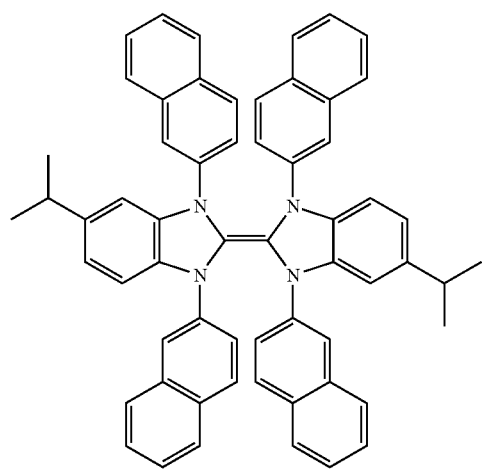
A10
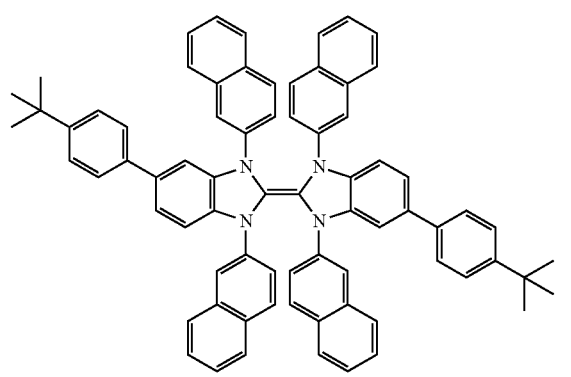
A11
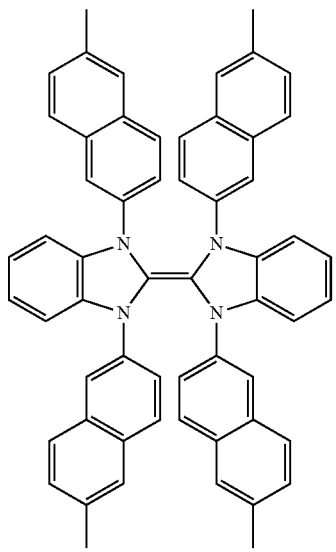
A12
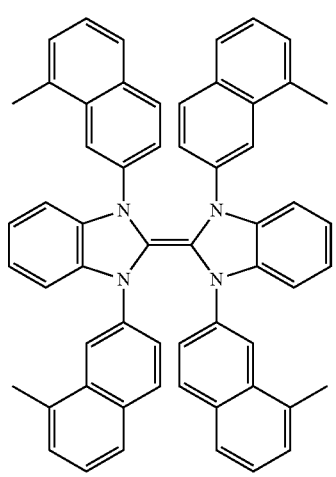
A13
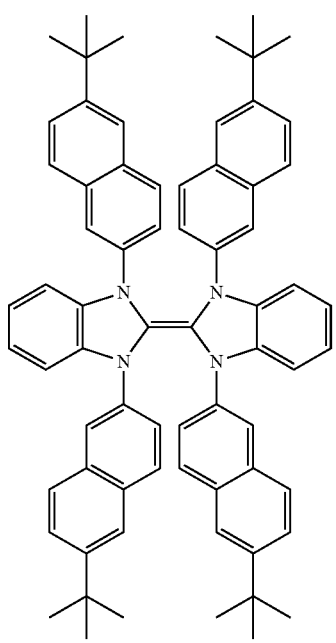

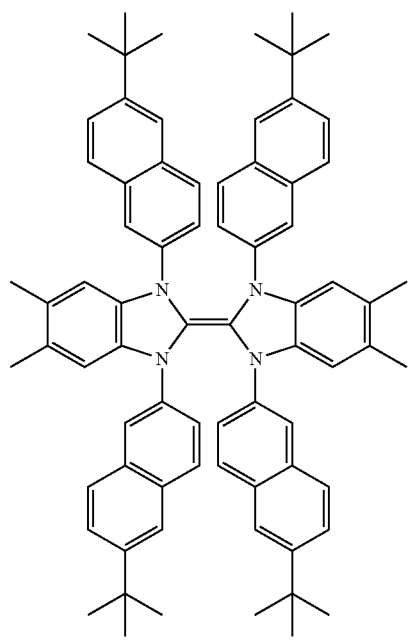
A14
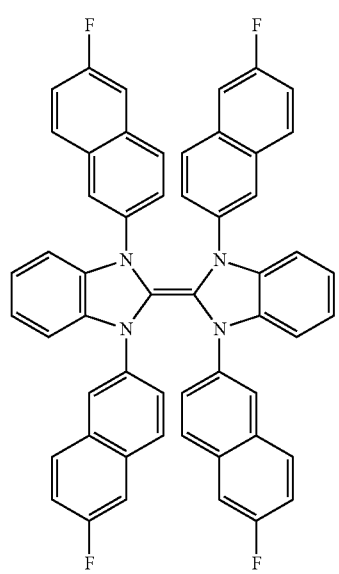
A15
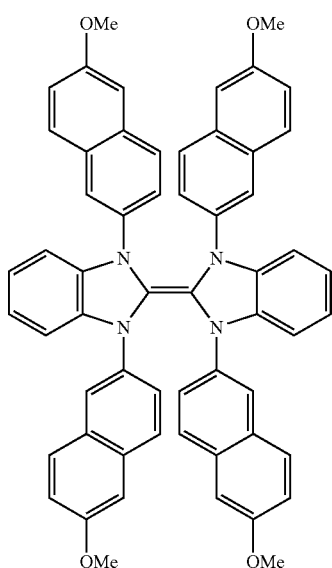
A17
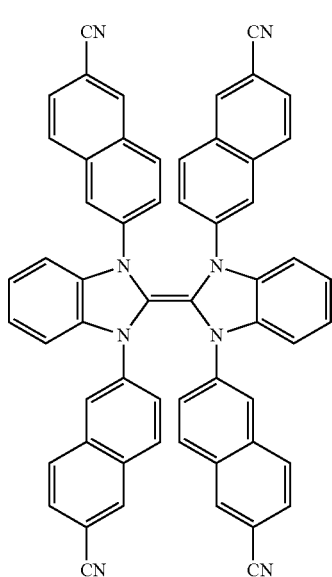
A18

A19
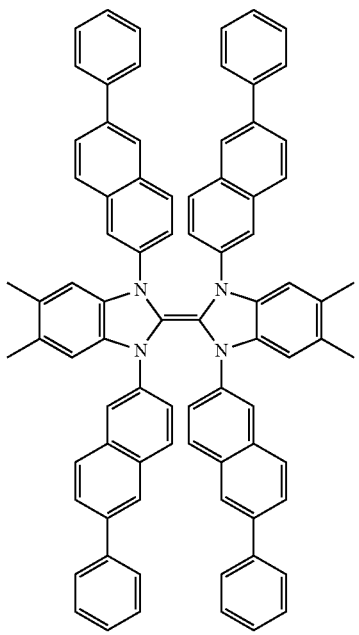
[Chem. 10]
B1
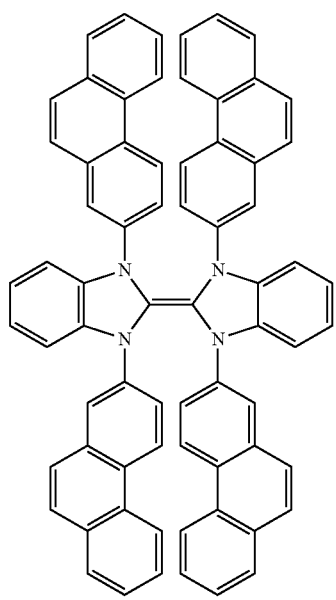
A20
B2

B3
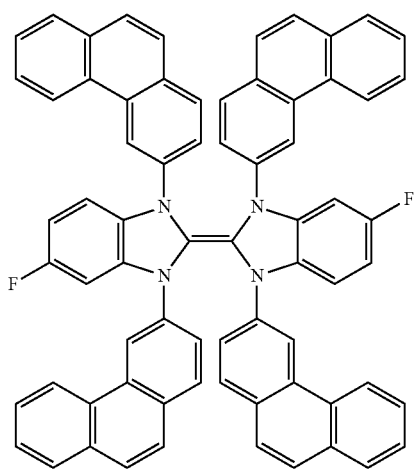
B4
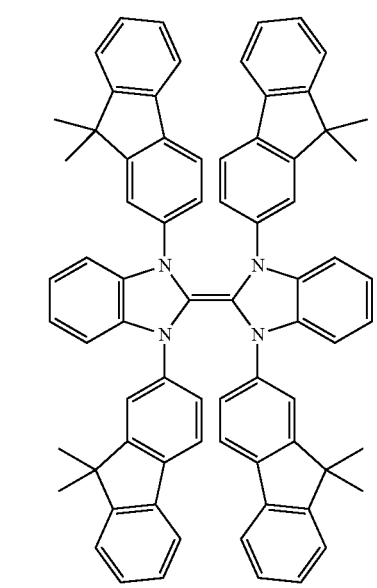
B5
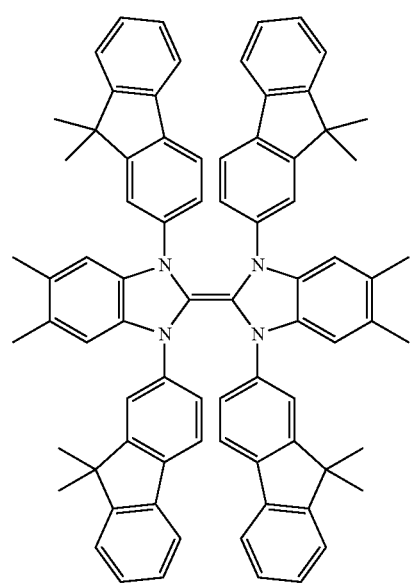
B6
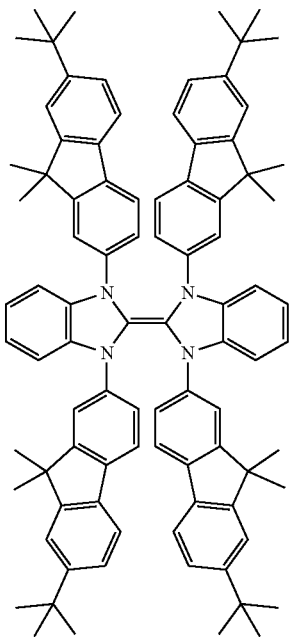
B7
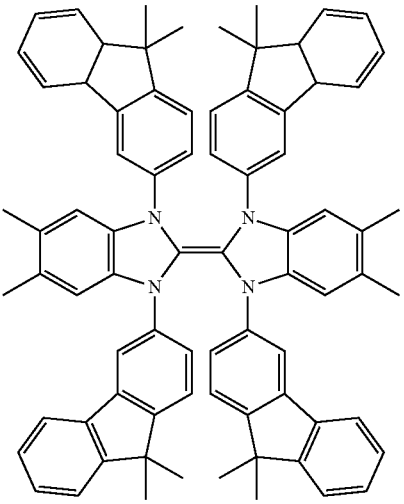

B8
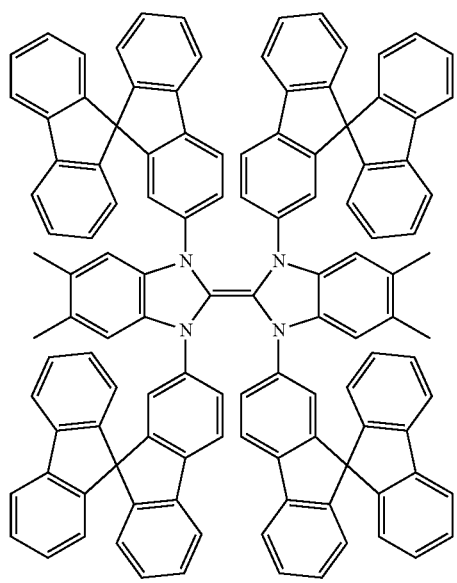
B5
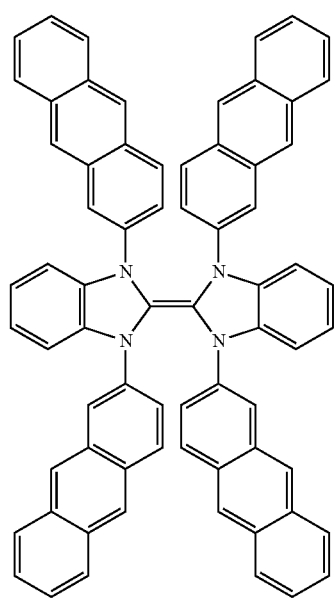
B6
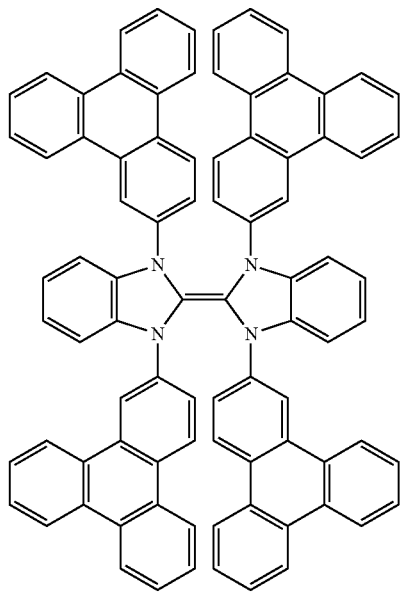
B7
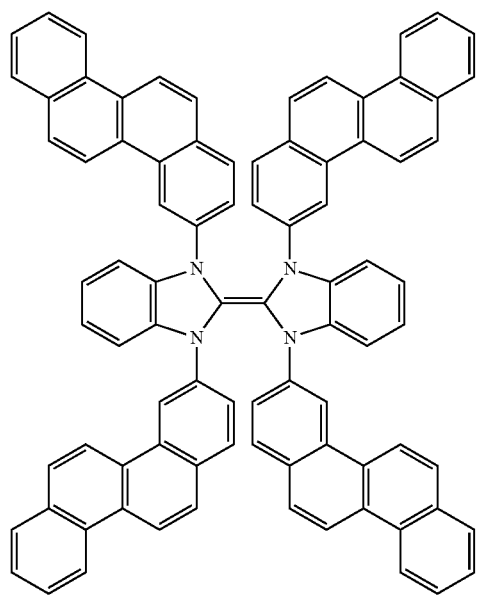

-continued
B8
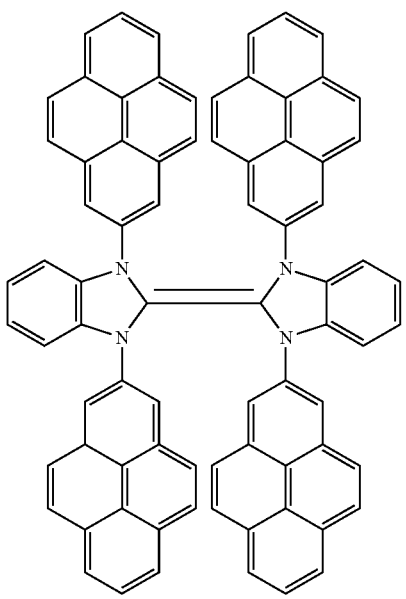
[Chem. 11]
C1
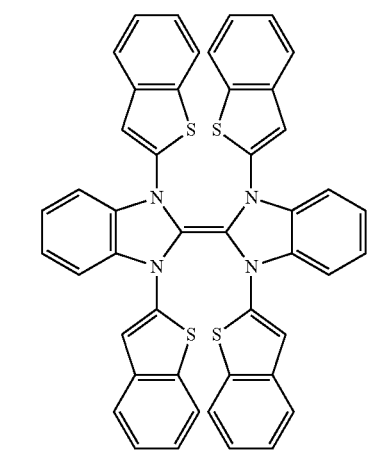
C2
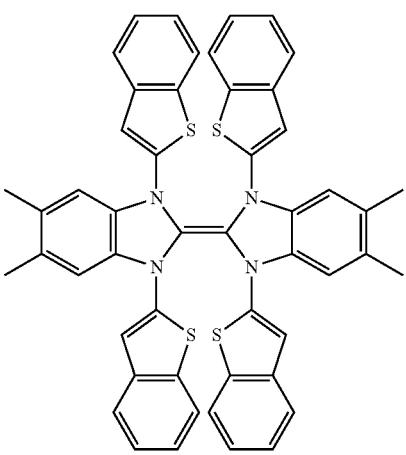
-continued
C3
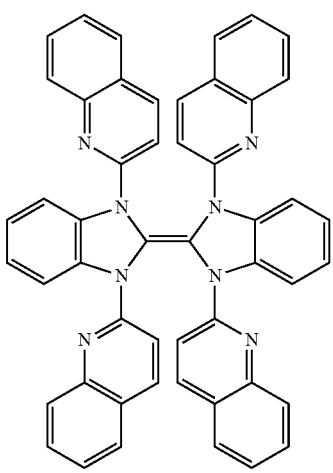
C4
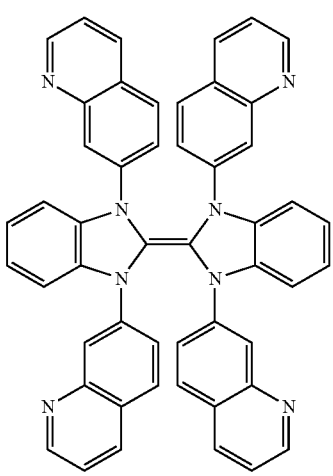
C5
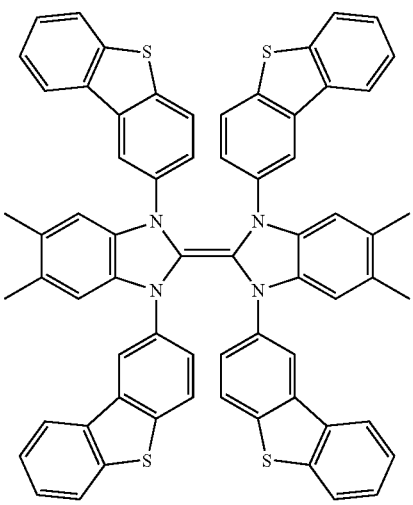

25
-continued
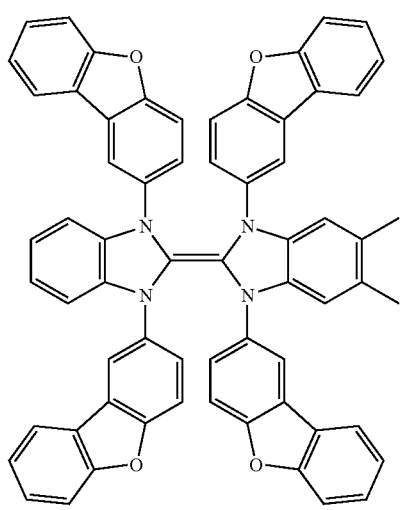
C6
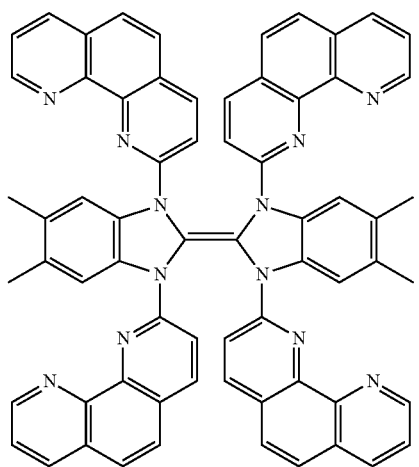
C7
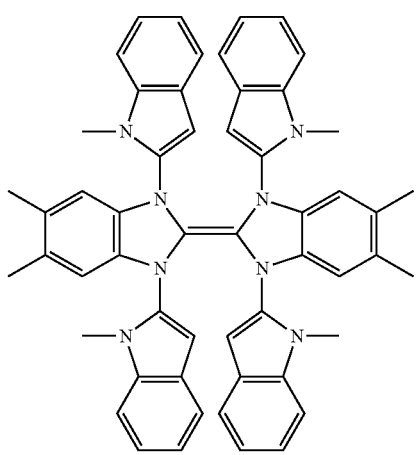
C8
26
-continued
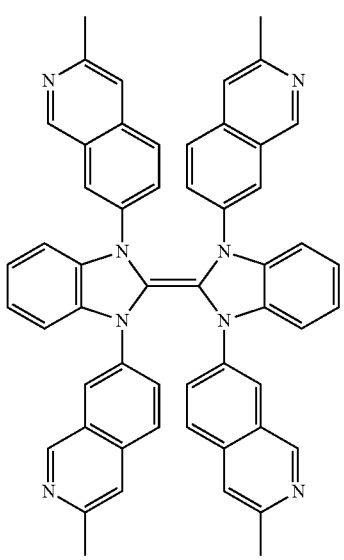
C9
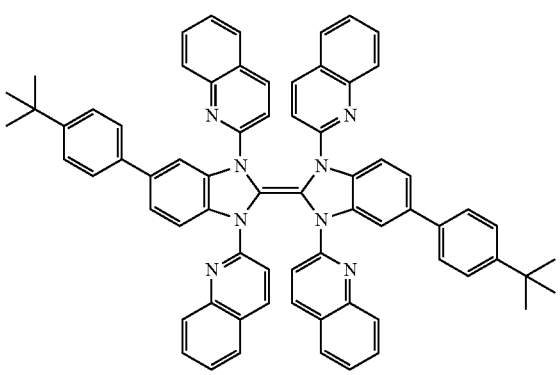
C10
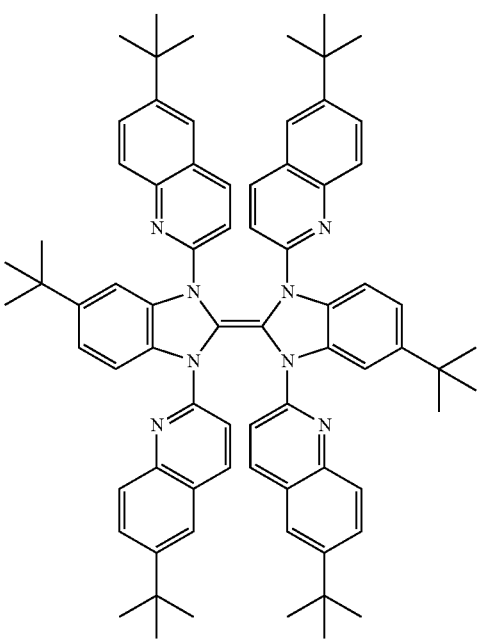
C11

C12

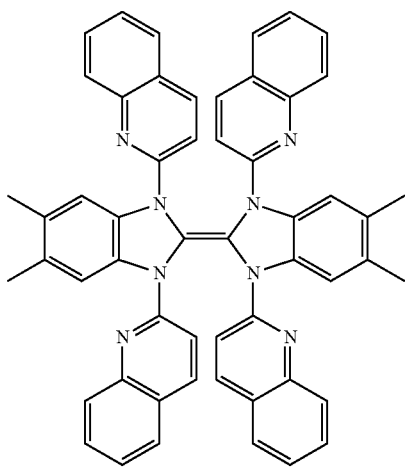

C13

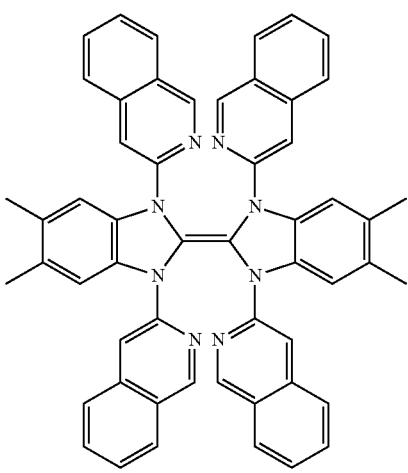

C14

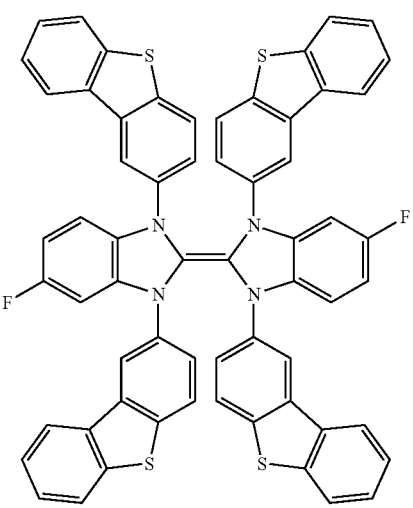

C15

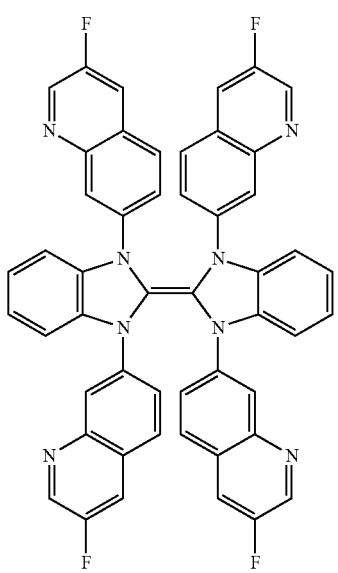

C16

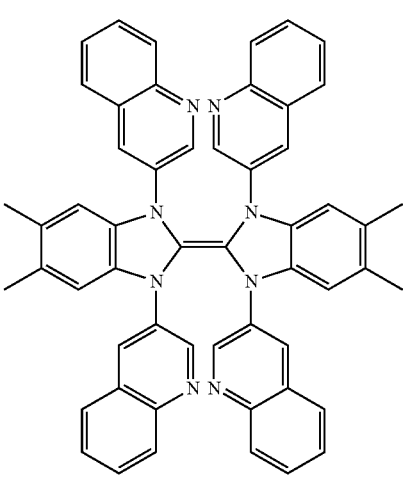

The organic compounds in Group A each have substituted or unsubstituted 1-naphthyl groups as the condensed rings represented by $Ar_1$ to $Ar_4$ in General Formula (1). These compounds are such that the 1,1',3,3'-tetrahydro-2,2'-bibenzo[d]imidazolidene skeleton has condensed rings having as low a molecular weight as possible as the substituents from the viewpoint of the stability to oxidation and the sublimability.

In other words, the organic compounds in Group A each balance stability with sub-limability because of the presence of 2-naphthyl groups as the condensed rings represented by $Ar_1$ to $Ar_4$ in General Formula (1).

The organic compounds in Group B each have an aromatic hydrocarbon having 3 rings or more as the condensed rings represented by $Ar_1$ to $Ar_4$ in General Formula (1). Since bulkier aromatic rings are present around the nitrogen atoms, this structure can provide more stable compounds.

In other words, the organic compounds in Group B are more stable because of the presence of aromatic hydrocarbons having 3 rings or more as the condensed rings represented by $Ar_1$ to $Ar_4$ in General Formula (1).

The organic compounds in Group C each have substituted or unsubstituted condensed rings containing a heteroatom as the substituents represented by $Ar_1$ to $Ar_4$ in General Formula (1). Such a structure having heteroatoms not only sterically stabilizes the compound, but also electrically influences the nitrogen atoms to vary the oxidation potential, thus improving the stability of the organic compound.

In other words, the organic compounds in Group C are highly stable because of the presence of the condensed rings containing a heteroatom as the substituents represented by $Ar_1$ to $Ar_4$ in General Formula (1).

[Synthesis of 2,2'-bibenzo[d]imidazolidene Compound Having Condensed Rings at the 1-, 1'-, 3- and 3'-Positions]

A process for synthesizing the present organic compound will now be described. The present organic compound may be synthesized according to the following reaction scheme. In the following reaction scheme, $R_1$ and $R_2$ are substituents to be introduced.

[Chem.12]

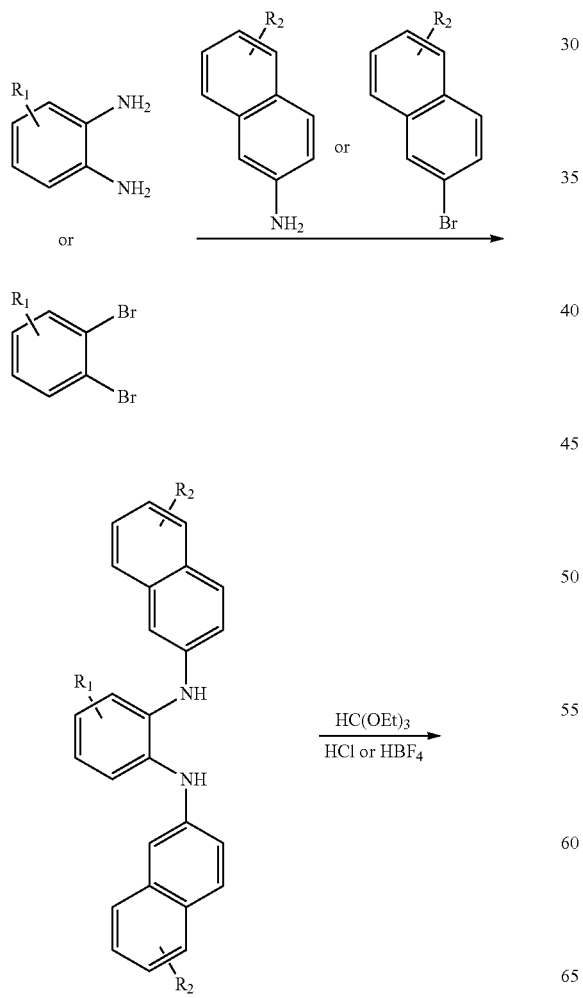

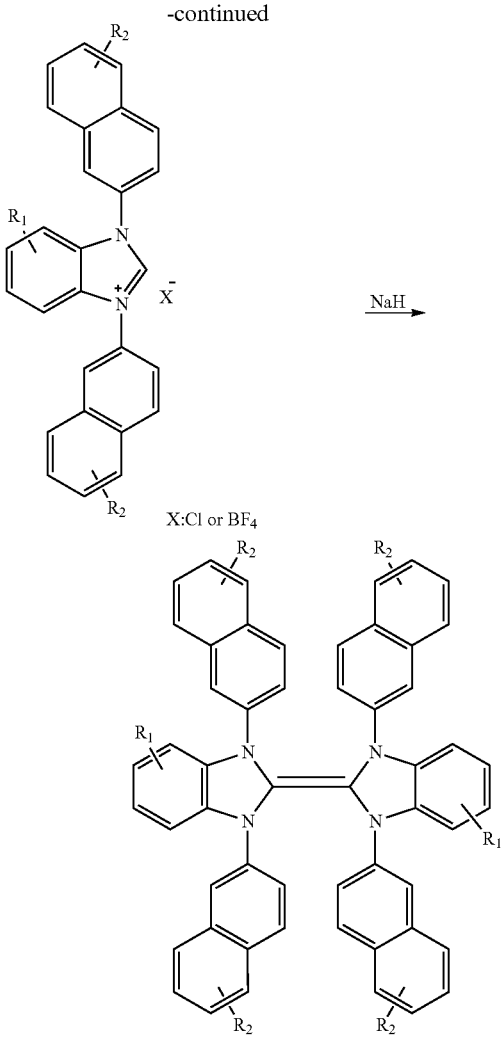

Organic Electronic Element

The organic electronic element includes a pair of electrode, and an organic compound layer between the electrodes. The organic compound layer contains an organic compound expressed by General Formula (1).

The organic electronic element of the present embodiment may be an organic light-emitting element, an organic transistor, or an organic solar cell. A single organic compound layer may be used, or a plurality of organic compound layers may be used. The organic compound expressed by General Formula (1) may be used in any of the organic compound layers.

The organic light-emitting lement according to an embodiment includes an anode and a cathode, and a luminescent layer between the anode and the cathode, and further includes an organic compound layer between the cathode and the luminescent layer. The organic compound layer contains an organic compound expressed by General Formula (1).

The organic light-emitting element may further include a hole injection layer, a hole transport layer, an electron blocking layer, a hole blocking layer, an electron transport layer, an electron injection layer, and other layers in addition to the luminescent layer. Also, the luminescent layer may be composed of a single layer or include a plurality of layers.

In the organic light-et ting element of the present embodiment, at least one layer disposed between the cathode and the luminescent layer contains the present organic compound.

More specifically, any of the luminescent layer, the hole blocking layer, the electron transport layer, the electron injection layer, and the like contains the present organic compound. Advantageously, the present organic compound is contained mainly in at least one of the electron injection layer and the electron transport layer, desirably in the electron injection layer.

In the present embodiment, the organic compound layers disposed between the cathode and the luminescent layer are referred to as the electron transport layer and the electron injection layer, and the organic compound layer in contact with the cathode is referred to as the electron injection layer.

Although the present organic compound may be used solely, it is advantageous to be used as a mixture with another compound (hereinafter referred to as the additional compound).

In this instance, the content of the additional compound may be in the range of more than 0% by weight to 80% by weight, relative to the total weight of the luminescent layer of the organic compound layers. For example, in the case where an electron transport layer and an electron injection layer are disposed between the cathode and the luminescent layer, the content of the additional compound is in the range of more than 0% by weight to 80% by weight, relative to the total weight of the electron injection layer. The electron transport layer is not considered for the calculation of the total weight.

The content of the additional compound can be estimated by subjecting the organic compound layer containing the present organic compound to TOF-SIMS or the like. Alternatively, the additional organic compound extracted from the organic light-emitting element may be measured with IR or UV or by NMR.

The additional compound desirably has a higher oxidation potential than the present organic compound.

Desirably, the additional compound may be an anthraquinone derivative, a fluorene derivative, a naphthalene derivative, an indene derivative, a terphenyl derivative, an acenaphthofluoranthene derivative, an indenoperylene derivative, or a phenanthroline derivative.

The organic light-emitting element may have any one of the following multilayer structure including one or more organic compound layers on a substrate.

(1) anode/luminescent layer/cathode
(2) anode/hole transport layer/luminescent layer/electron transport layer/cathode
(3) anode/hole transport layer/luminescent layer/electron transport layer/electron injection layer/cathode
(4) anode/hole injection layer/hole transport layer/luminescent layer/electron transport layer/cathode
(5) anode/hole injection layer/hole transport layer/luminescent layer/electron transport layer/electron injection layer/cathode
(6) anode/hole transport layer/electron blocking layer/luminescent layer/hole blocking layer/electron transport layer/cathode These are merely basic structures and are not intended to limit the structure of the organic light-emitting element containing the present organic compound.

The organic light-emitting element may take various structures. For example, the organic light-emitting element of an embodiment may further include an insulating layer between an electrode and an organic compound layer, or may have an adhesion layer or an interference layer. The electron transport layer or the hole transport layer may be composed of two layers having different ionization potentials, or the luminescent layer may be composed of two layers containing different luminescent materials.

The light-emitting element may be of a bottom emission type that emits light through the substrate, of a top emission type that emits light through the opposite side to the substrate, or of a type that emits light through both sides.

Among the above structures, structure (6) including both an electron blocking layer and a hole blocking layer is advantageous. Structure (6) enables holes and electrons to be confined in the luminescent layer without leaking the carriers, thus achieving an organic light-emitting element having high emission efficiency.

The luminescent layer of the organic light-emitting element of an embodiment may contain a plurality of constituents including a main constituent and sub constituents. The main constituent refers to the compound accounting for the highest percentage, on a weight basis, of the constituents in the luminescent layer, and may be referred to as the host material. The host material is a compound present around the molecules of a guest material as the matrix of the luminescent layer, and functions mainly to transport carriers and supply excitation energy to the guest material.

The sub constituents are compounds other than the main constituent. Sub constituents include a guest material, a luminescence assist material, and a charge injection material. The guest material may be called a dopant material. The luminescence assist material and the charge injection material may have the same structure or different structures. These compounds are sub constituents, but may be called host material 2 to distinguish from the guest material.

The guest material in the luminescent layer is a compound that functions for the major light emission.

The guest material content is in the range of 0.01% by weight to less than 50% by weight, preferably in the range of 0.1% by weight to less than 20% by weight, relative to the total weight of the compounds in the luminescent layer. Desirably, the guest material content is 10% by weight or less from the viewpoint of preventing concentration quenching. The guest material may be present uniformly throughout the layer made of the host material, or may be present with a concentration gradient. Alternatively, the layer of the host material may partially contain the guest material so as to have a portion not containing the guest material.

The luminescent layer may be defined by a single layer or may have a multilayer structure. Luminescent materials having two or more emission colors may be used for mixing colors. The multilayer structure refers to a state where different luminescent layers are formed one on top of another. In this instance, the organic light-emitting element may emit, but is not limited to, color light from blue to green or red.

For example, the organic light-emitting element may emit white light or intermediate color light. For emitting white light, the luminescent layer may emit red, blue or green. The layers of the organic light-emitting element may be formed by vapor deposition or coating.

In an embodiment, the luminescent layer of the organic light-emitting element may contain a plurality of luminescent materials. Any two of the plurality of luminescent materials may emit different light from each other, and the element containing these luminescent materials may emit white light.

The organic light-emitting element may include a plurality of luminescent layers, and one or some of the plurality of luminescent layers may emit light having a different wavelength from other luminescent layers. The colors of light from these luminescent layers may be mixed so that the organic light-emitting element can emit white light.

In the present embodiment, the hole blocking layer refers to a layer that blocks holes, and is disposed adjacent to the side of the luminescent layer closer to the cathode.

The present organic compound may be used in combination with a luminescent material of a low-molecular-weight compound or a polymer, a hole-injecting compound, a hole-transporting compound, a compound that can act as a host, a luminescent compound, an electron-injecting compound, or an electron-transporting compound, if necessary.

These compounds will now be described.

The hole-injecting or transporting material desirably has so high a hole mobility as facilitates hole injection from the anode and enables the injected holes to be transported to the luminescent layer. From the viewpoint of preventing the crystallization or any other deterioration of the material in the organic light-emitting element, the hole-injecting or transporting material desirably has a high glass transition temperature. Low-molecular-weight or polymeric hole-injecting or transporting materials include triarylamine derivatives, arylcarbazole derivatives, phenylenediamine derivatives, stilbene derivatives, phthalocyanine derivatives, porphyrin derivatives, poly(vinyl carbazole), polythiophene, and other conductive polymers. The hole-injecting or transporting material is also used suitably in the electron blocking layer.

Exemplary compounds that can be used as the hole-injecting or transporting material include, but are not limited to, the following.

[Chem.13]

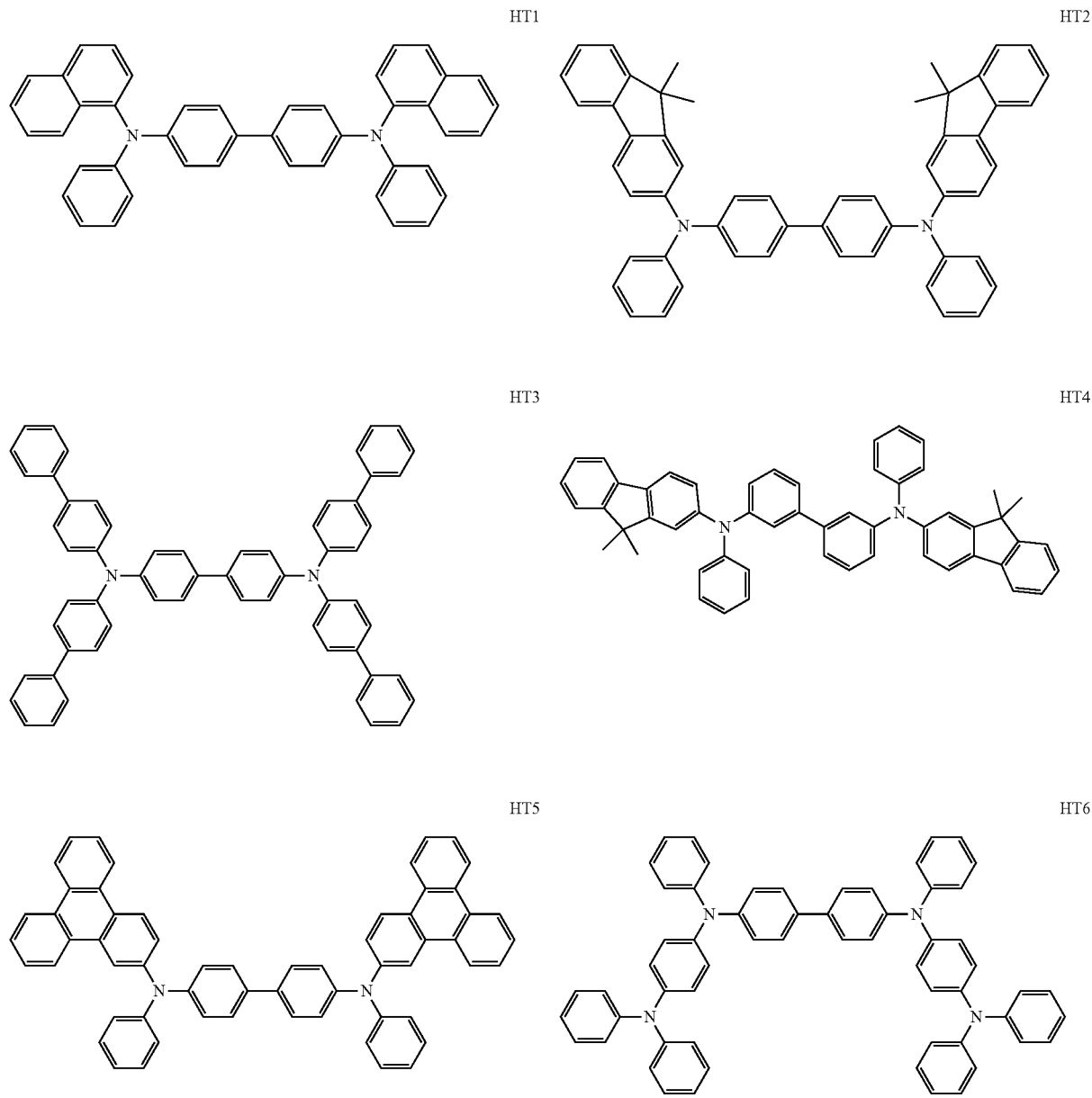

-continued
HT7
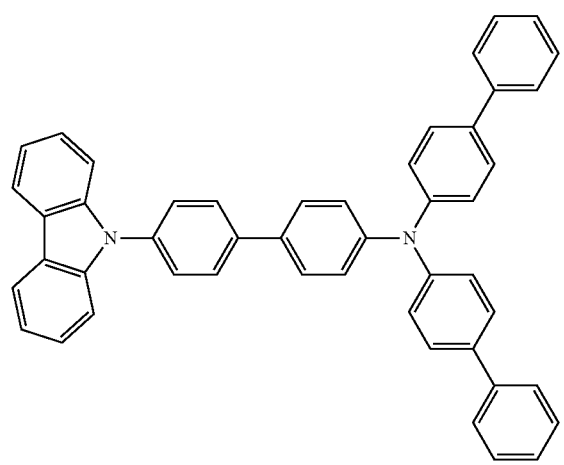
HT8
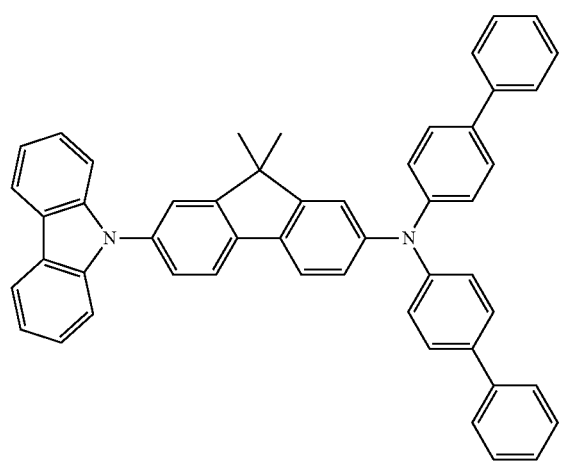
HT9
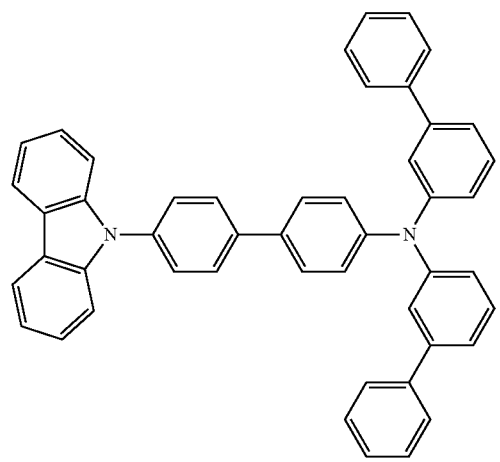
HT10
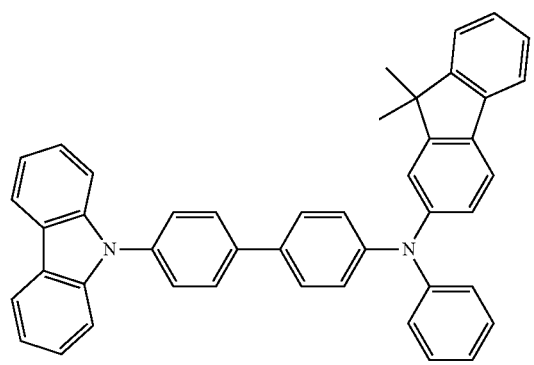
HT11
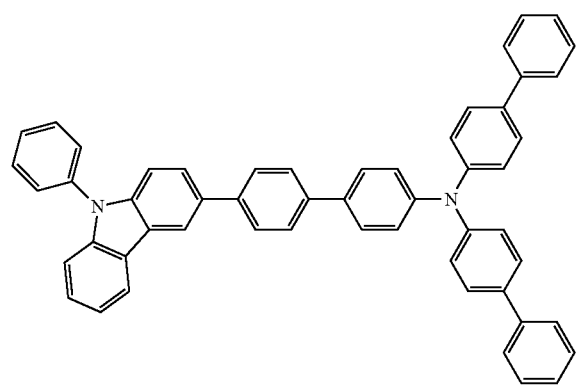
HT12
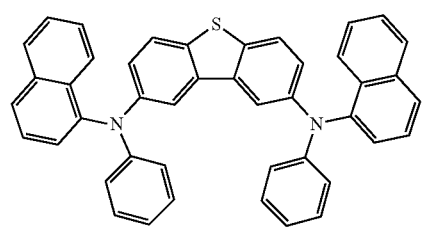

HT13

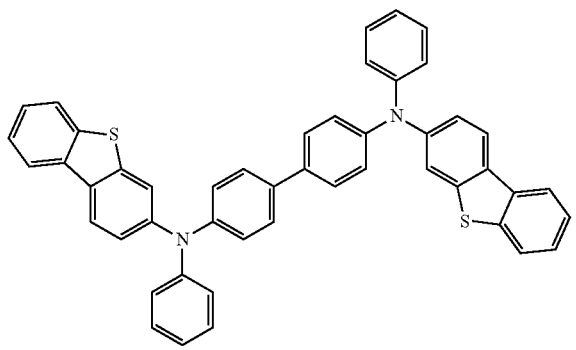

HT14

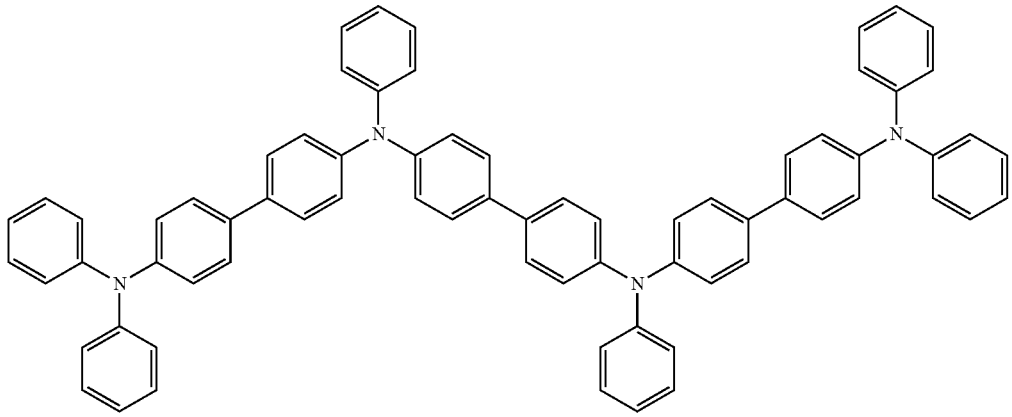

Luminescent materials involved in light emission include condensed ring compounds (such as fluorene derivatives, naphthalene derivatives, pyrene derivatives, perylene derivatives, tetracene derivatives, anthracene derivatives, and rubrene), quinacridone derivatives, coumarin derivatives, stilbene derivatives, and tris(8-quinolinolate) aluminum and other organic aluminum complexes, iridium complexes, platinum complexes, rhenium complexes, copper complexes, europium complexes, ruthenium complexes, and polymer derivatives such as poly(phenylene vinylene) derivatives, polyfluorene derivatives, and polyphenylene derivatives.

Exemplary compounds that can be used as the luminescent material include, but are not limited to, the following.

[Chem.14]

BD1

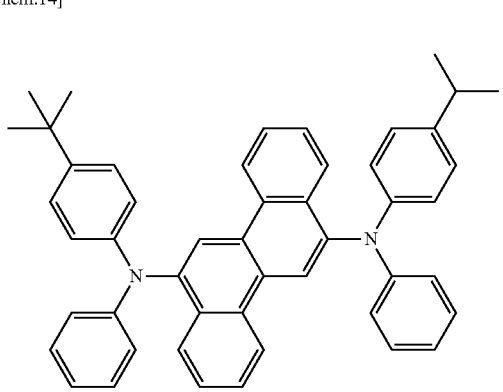

BD2

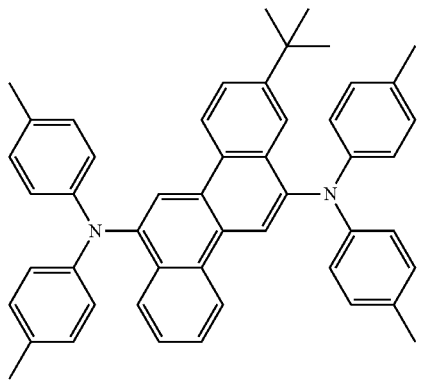

BD3

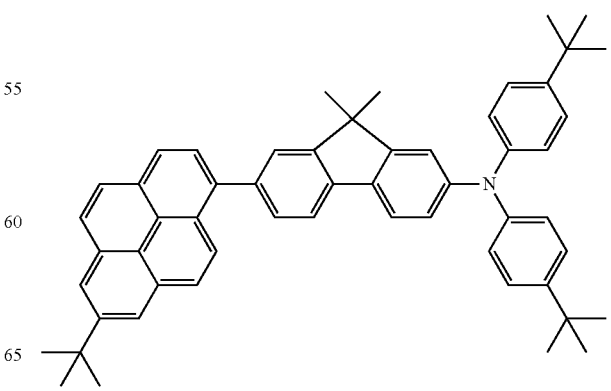

BD4
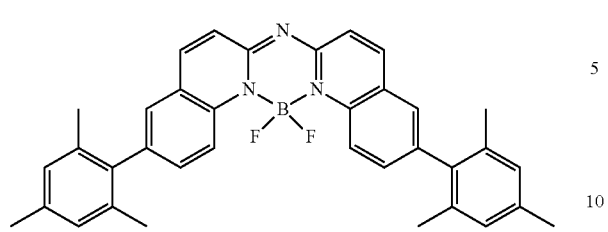
BD5
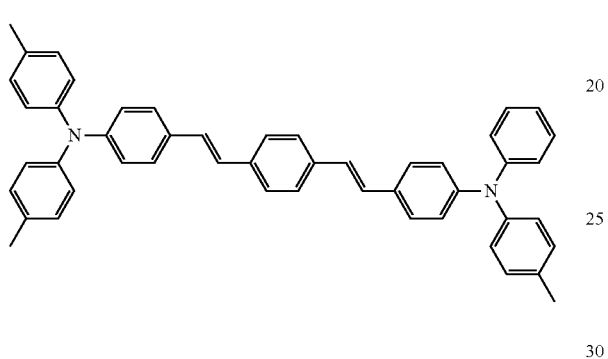
BD6
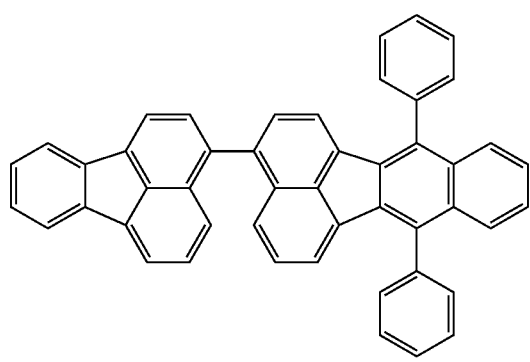
BD7
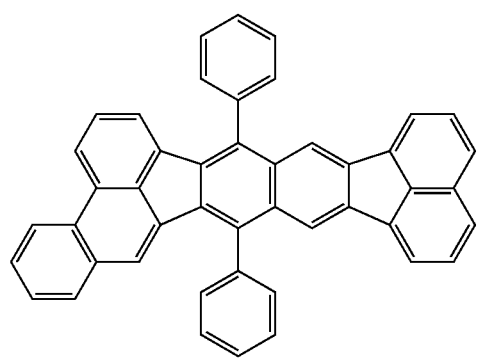
BD8
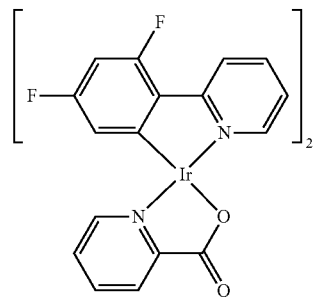
GD1
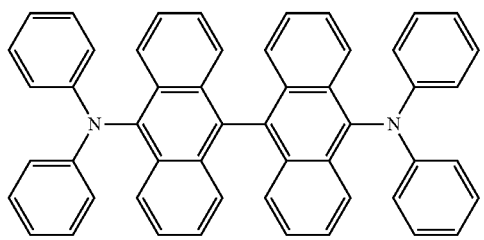
GD2
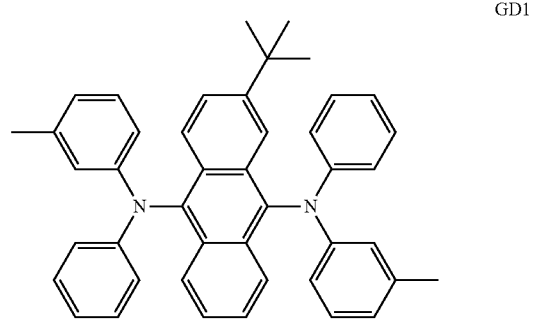
GD3
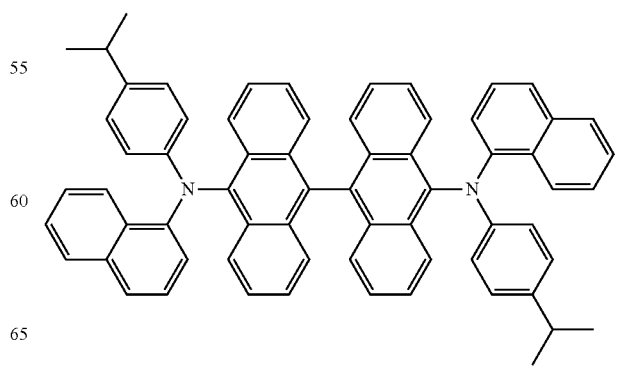

-continued
GD4
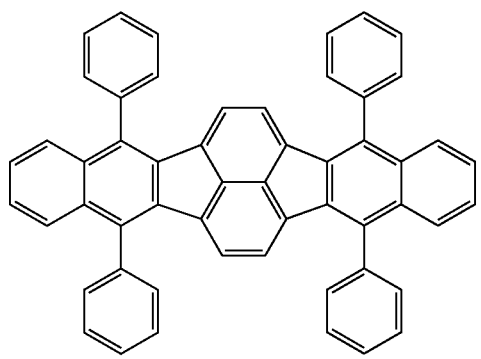
GD5
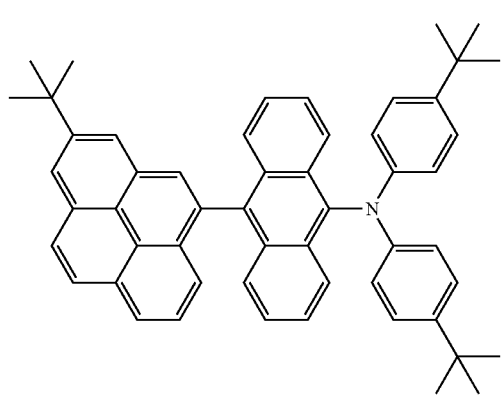
GD6
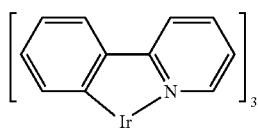
GD7
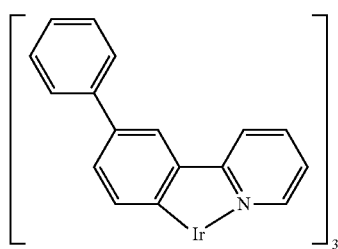
GD8
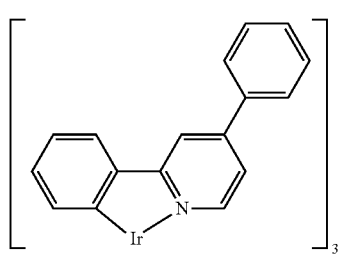
-continued
RD1
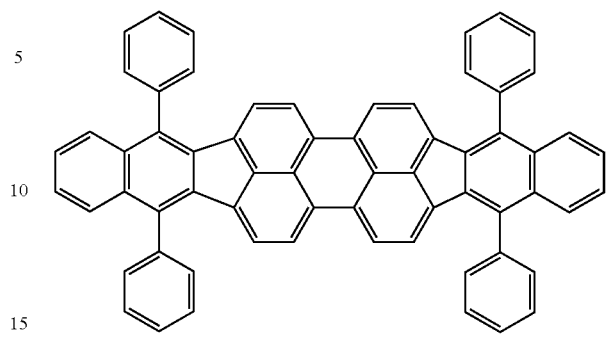
RD2
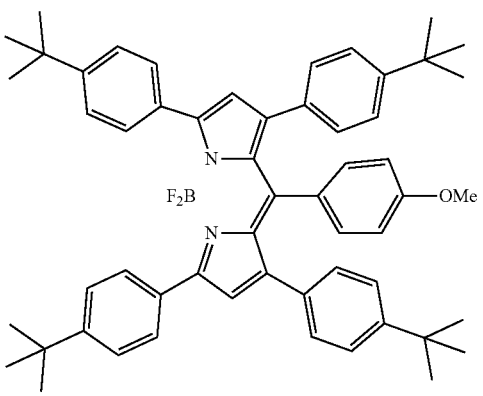
RD3
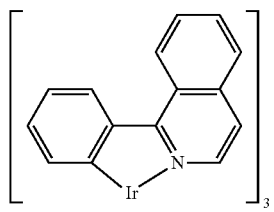
RD4
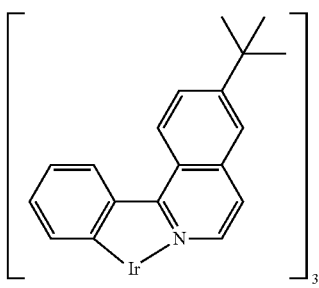
RD5
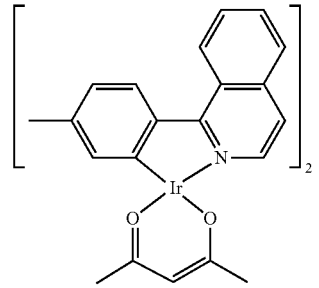

RD6

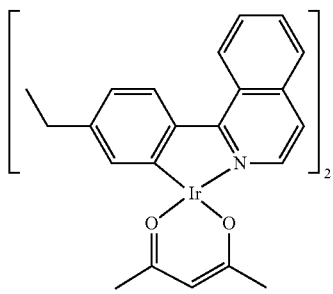

RD7

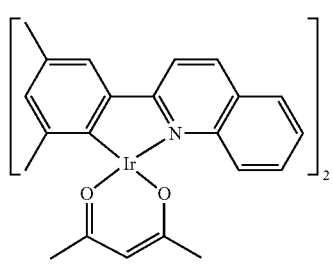

RD8

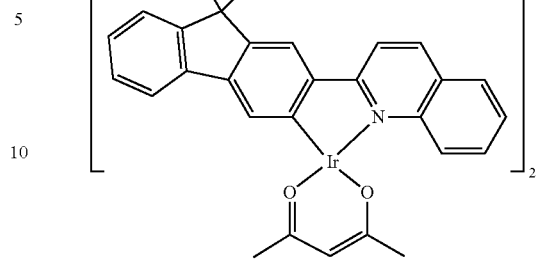

Host or luminescence assist materials that can be used in the luminescent layer include aromatic hydrocarbons and derivatives thereof, carbazole derivatives, dibenzofuran derivatives, dibenzothiophene derivatives, organic aluminum complexes, such as tris(8-quinolinolate) aluminum, and organic beryllium complexes.

Exemplary compounds that can be used as the host or luminescent assist material include, but are not limited to, the following.

[Chem.15]

EM1

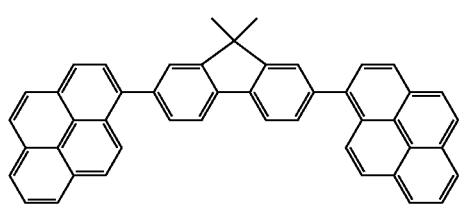

EM2

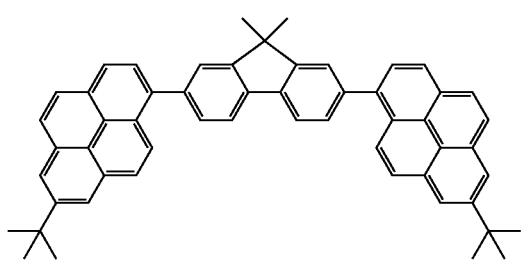

EM3

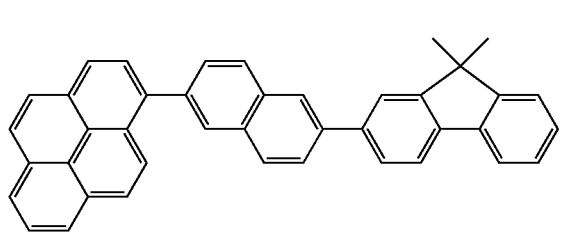

EM4

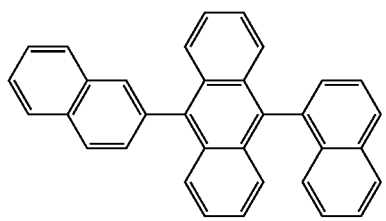

EM5

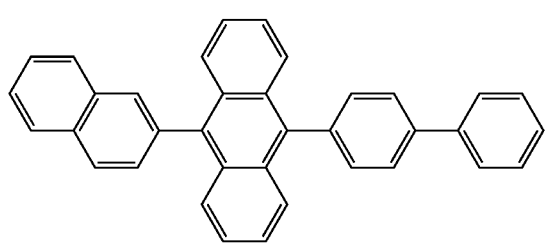

EM6

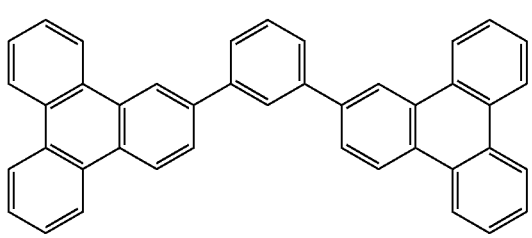

-continued
EM7
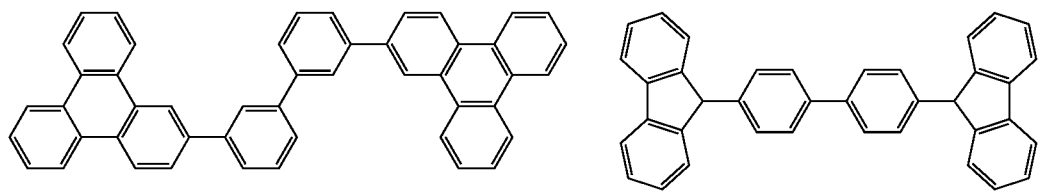
EM8
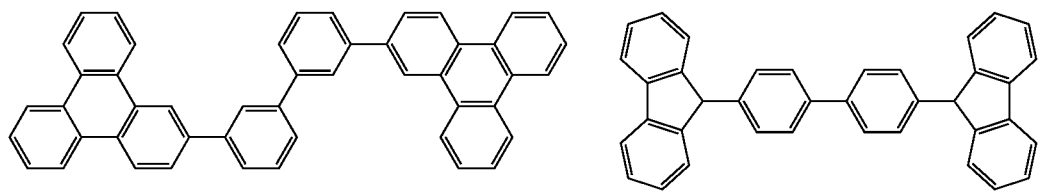
EM9
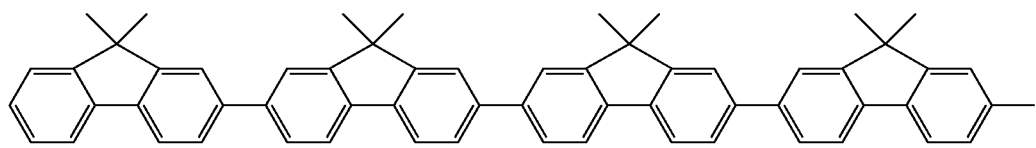
EM10
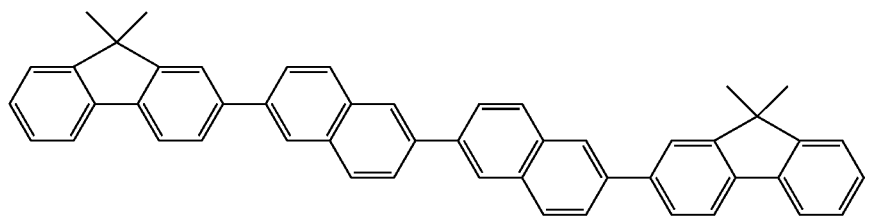
EM11
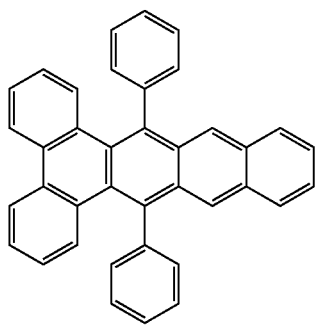
EM12
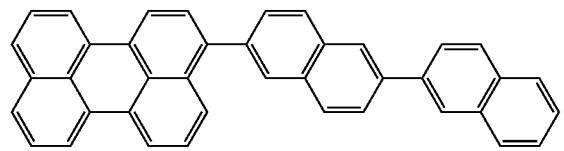
EM13
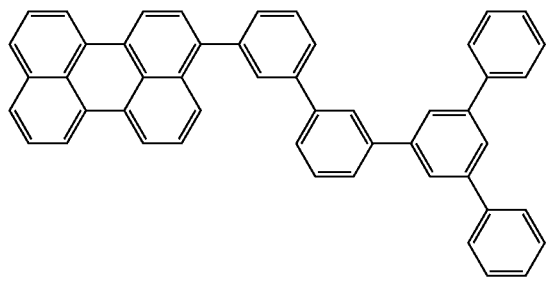
EM14
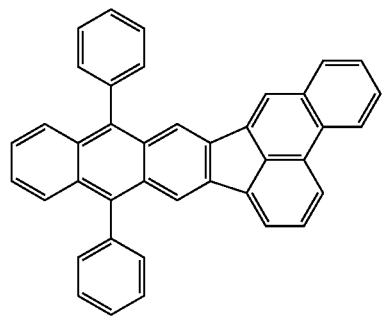
EM15
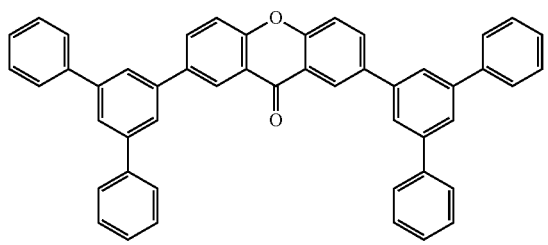
EM16
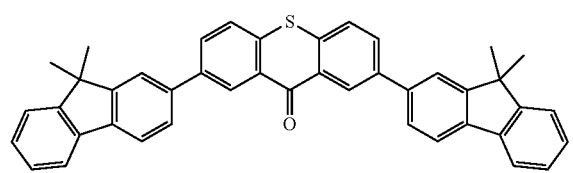

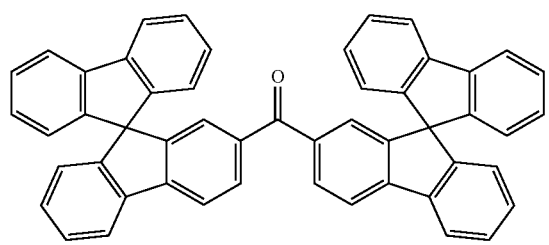

EM17

The electron-transporting material can be selected from the compounds capable of transporting electrons injected from the cathode to the luminescent layer in view of the balance with the hole mobility of the hole-transporting material. Electron-transporting materials include oxadiazole derivatives, oxazole derivatives, pyrazine derivatives, triazole derivatives, triazine derivatives, quinoline derivatives, quinoxaline derivatives, phenanthroline derivatives, organic aluminum complexes, and condensed ring compounds (such as fluorene derivatives, naphthalene derivatives, chrysene derivatives, and anthracene derivatives). These electron-transporting materials are also used suitably in the hole blocking layer.

Exemplary compounds that can be used as the electron-transporting material include, but are not limited to, the following.

[Chem.16]

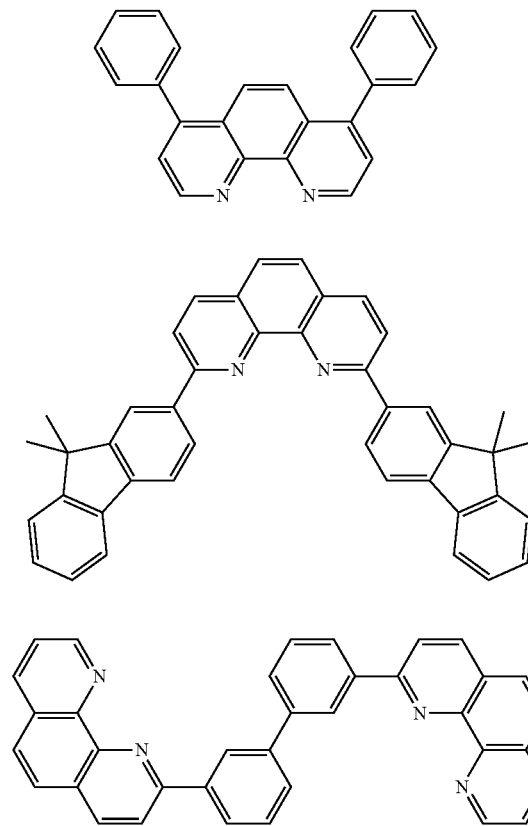

ET1

ET2

ET3

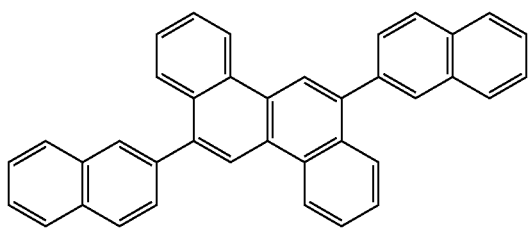

ET4

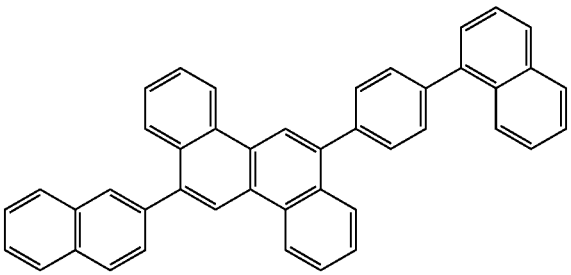

ET5

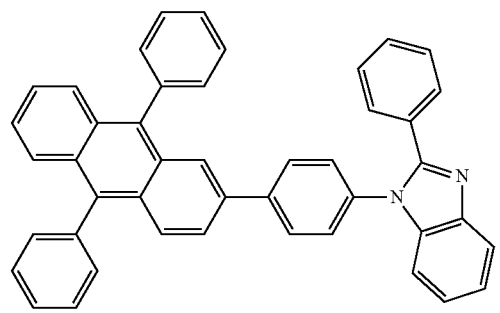

ET6

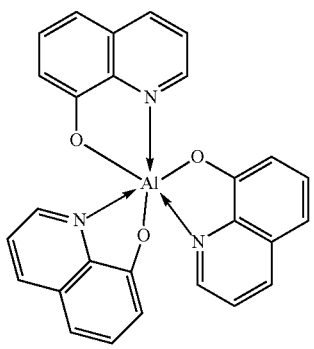

ET7

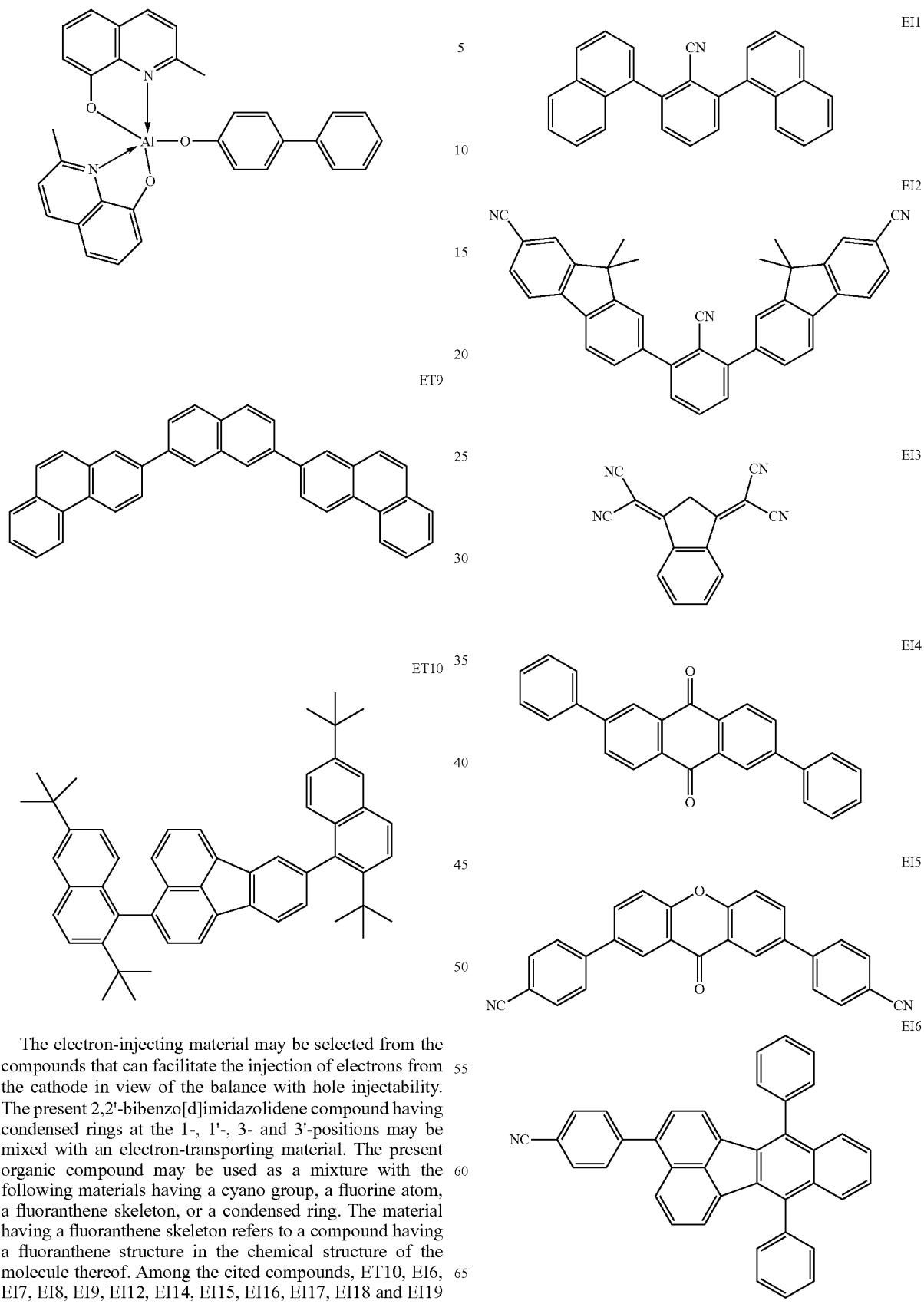

The electron-injecting material may be selected from the compounds that can facilitate the injection of electrons from the cathode in view of the balance with hole injectability. The present 2,2'-bibenzo[d]imidazolidene compound having condensed rings at the 1-, 1'-, 3- and 3'-positions may be mixed with an electron-transporting material. The present organic compound may be used as a mixture with the following materials having a cyano group, a fluorine atom, a fluoranthene skeleton, or a condensed ring. The material having a fluoranthene skeleton refers to a compound having a fluoranthene structure in the chemical structure of the molecule thereof. Among the cited compounds, ET10, EI6, EI7, EI8, EI9, EI12, EI14, EI15, EI16, EI17, EI18 and EI19 are compounds having a fluoranthene structure.

-continued
EI7
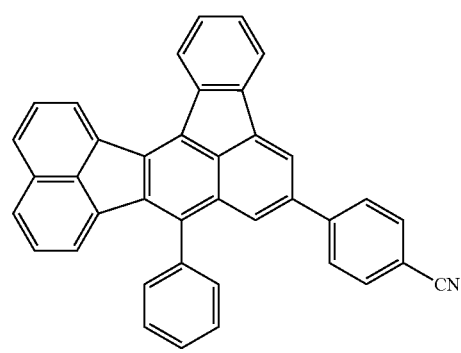
EI8
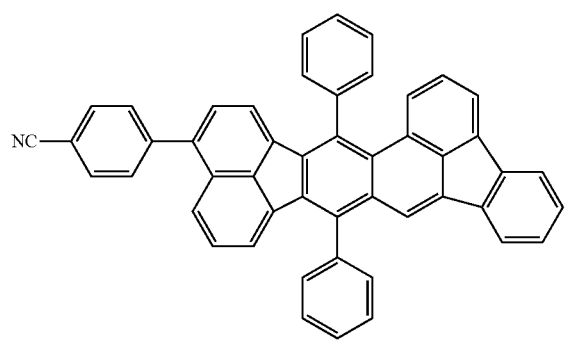
EI9
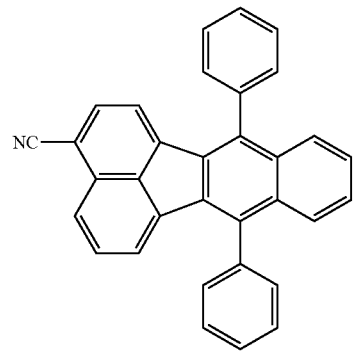
EI10
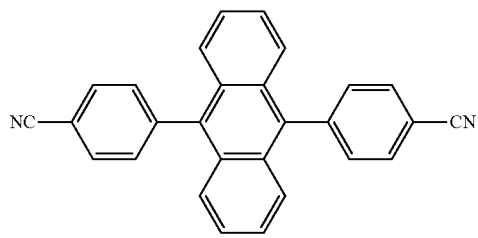
EI11
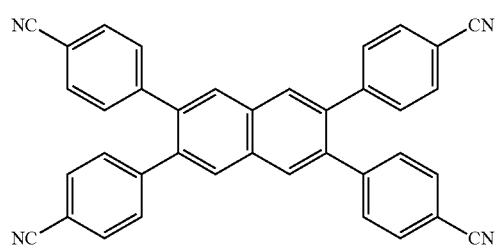
-continued
EI12
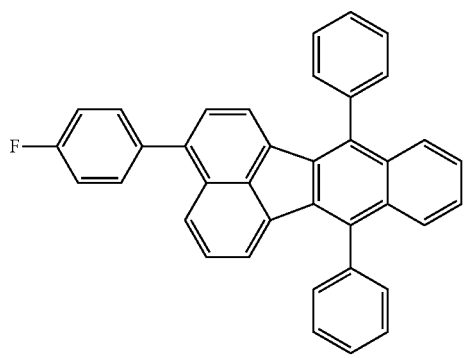
EI13
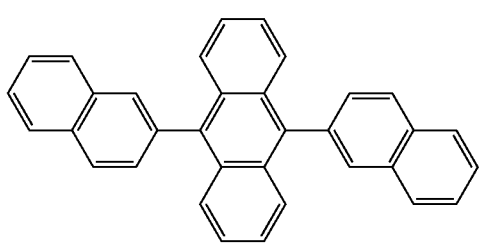
EI14
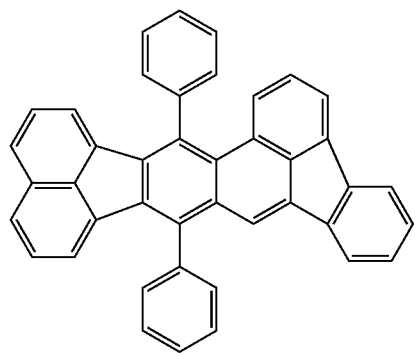
EI15
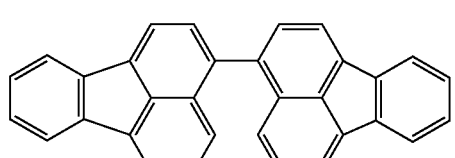
EI16
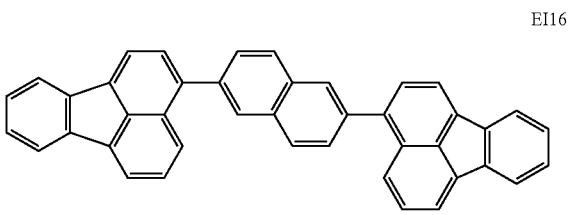

EI17
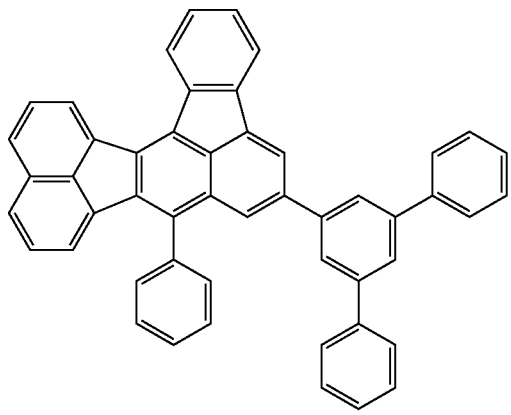

EI18
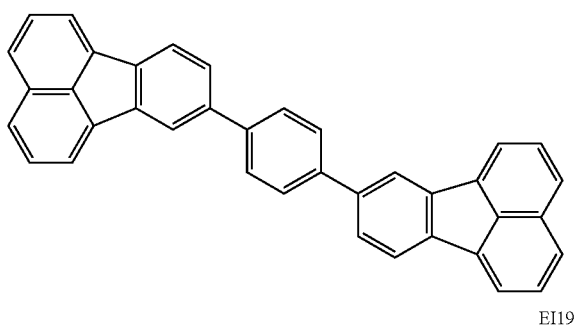

EI19
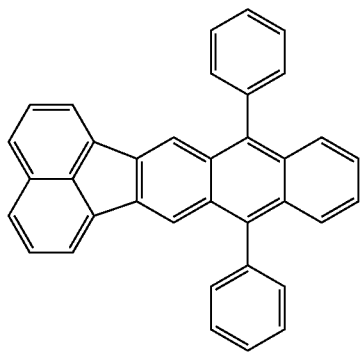

EI20
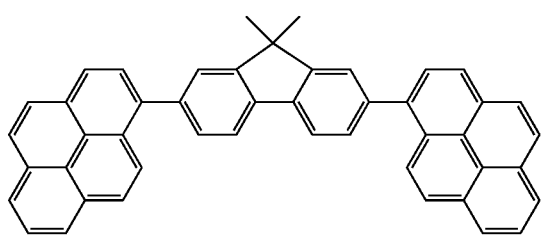

The anode is desirably made of a compound having as high a work function as possible. Such materials include simple metals, such as gold, platinum, silver, copper, nickel, palladium, cobalt, selenium, vanadium, and tungsten, and mixtures therewith or alloys thereof; and metal oxides, such as tin oxide, zinc oxide, indium oxide, indium tin oxide (ITO), and zinc indium oxide. Electrically conductive materials can also be used, such as polyaniline, polypyrrole, and polythiophene.

These electrode materials may be used singly or in combination. The anode may be composed of a single layer or a plurality of layers.

On the other hand, the cathode is desirably made of a compound having a low work function. Examples of the cathode material include alkali metals, such as lithium; alkaline-earth metals, such as calcium; and other simple metals such as aluminum, titanium, manganese, silver, lead, and chromium, and mixtures therewith. Alloys of these simple metals may be used. Examples of such an alloy include magnesium-silver, aluminum-lithium, aluminum-magnesium, silver-copper, and zinc-silver. A metal oxide, such as indium tin oxide (ITO), may be used. These electrode materials may be used singly or in combination. The cathode may be composed of a single layer or a plurality of layers.

The organic compound layers (hole injection layer, hole transport layer, electron blocking layer, luminescent layer, hole blocking layer, electron transport layer, electron injection layer, etc.) of the organic light-emitting element of the present embodiment may be formed by the following process.

The organic compound layers of the organic light-emitting element may be formed in a dry process performed by, for example, vacuum deposition, ionized deposition, sputtering, or using plasma. Alternatively, the organic compound layers may be formed in a wet process performed by a known coating method using a material dissolved in a solvent, such as spin coating, dipping, a cast method, Langmuir-Blodgett (LB) method, or an ink jet method.

Layers formed by vacuum deposition, solution coating or the like are unlikely to crystallize and are thus superior in stability with time. For the coating method, an appropriate binder resin may be used in combination.

Examples of the binder resin include, but are not limited to, polyvinylcarbazole resin, polycarbonate resin, polyester resin, ABS resin, acrylic resin, polyimide resin, phenol resin, epoxy resin, silicone resin, and urea resin.

These binder resins may be used in the form of homopolymer or copolymer as a single material, or may be used in combination in the form of mixture. Other known additives, such as a plasticizer, an antioxidant, and an ultraviolet light adsorbent, may further be used, if necessary.

Applications of Organic Light-Emitting Element

The organic light-emitting element of the present embodiment can be used for a display device or a lighting device. In addition, the organic light-emitting element may be used as an exposure light source of an electrophotographic image forming apparatus, a back light of a liquid crystal display device, or a light-emitting device including a white light source provided with a color filter. The color filter may transmit at least one color of red, green and blue.

The display device according to an embodiment includes a plurality of pixels, and at least one of the pixels includes the organic light-emitting element according to the present enibodiment. The pixels may be called emission points. Each of the pixels includes the organic light-emitting element and an active element. The active element may be a switching element or an amplifier element. More specifically, the active element may be a transistor. Either the anode or the cathode of the organic light-emitting element is electrically connected to either the drain or the source electrode of the transistor. The transistor may contain an oxide semiconductor in the active region thereof. The oxide semiconductor may be amorphous or crystalline, or may contain amorphous phases and crystalline phases. The crystalline phases may be monocrystalline or microcrystalline, or may be oriented in a specific axis, such as the C-axis. Crystalline phases in two or more of these states may be mixed.

An organic light-emitting device including such a switching element may be used as an image display unit in which organic light-emitting elements act as pixels, or may be used as a lighting device. Alternatively, the organic light-emitting device may be used as an exposure light source of an electrophotographic image forming apparatus, such as a laser beam printer or a copy machine.

The display device may be used as an image display unit of a PC or the like. The transistor may be a TFT element. The TFT element may be formed on the insulating surface of a substrate.

Alternatively, the display device may be used in an image information processing apparatus that includes an input portion to which image information is input from an area CCD, a linear CCD, a memory card or the like and an information processing portion adapted to process the inputted information, and that thus displays the inputted information on a display portion.

The display portion of an image sensing device or an ink jet printer may have a function as a touch panel. The touch panel function may be operated by, but not limited to, a scheme using infrared, capacitance, resistive film, or electromagnetic induction.

Also, the display device may be used as a display portion of a multifunction printer.

The lighting device illuminates, for example, a room. The lighting device may emit white light (having a color temperature of 4200 K), neutral white light (having a color temperature of 5000 K), or any other color light from blue to red. At least any one of the organic light-emitting elements in the lighting device is the organic light-emitting element of an embodiment of the present invention.

The lighting device according to an embodiment includes the organic light-emitting element of the present embodiment and an AC/DC converter connected to the organic light-emitting element. The AC/DC converter converts alternating voltage into direct voltage. This converter is a circuit adapted to supply a driving voltage to the organic light-emitting element. The lighting device may further include a color filter.

The lighting device may include a heat radiation portion. The heat radiation portion is intended to dissipate heat from the device and may be made of, for example, a metal having a high specific heat or liquid silicon.

The image forming apparatus according to an embodiment of the present invention includes a photosensitive member, an exposure portion that exposes the photosensitive member, a charging member that charges the photosensitive member, and a developing portion that applies a developer to the photosensitive member. In the image forming apparatus, the exposure portion includes a plurality of organic light-emitting elements of the present embodiment. The developer may be a toner or an ink. The toner may be dry or liquid.

The organic light-emitting element of the present embodiment can be used as a member of an exposure unit for exposing the photosensitive member. The exposure unit may have a plurality of emission points, and at least any one of the emission points includes the organic light-emitting element of the present embodiment. The emission points are arranged in a line along the longitudinal direction of the photo-sensitive member.

The display device according to an embodiment of the present invention will now be described with reference to a figure. FIG. 1 is a schematic sectional view of a display device including organic light-emitting elements and TFT elements connected to the corresponding organic light-emitting elements. The TFT elements are active elements.

The display device 1 shown in FIG. 1 includes a substrate 11 made of glass or the like, and a moisture-proof layer 12 over the substrate for protecting TFT elements or organic compound layers. Reference numeral 13 designates a metal gate electrode 13. Reference numeral 14 designates a gate insulating film 14, and reference numeral 15 designates a semiconductor layer.

Each TFT element 18 includes the semiconductor layer 15, a drain electrode 16, and a source electrode 17. An insulating film 19 is disposed over the TFT elements 18. Each source electrode 17 is connected to the anode 21 of the corresponding organic light-emitting element through a contact hole 20.

The electrical connection from the electrode (anode or cathode) of the organic light-emitting element to the electrode (source electrode or drain electrode) of the TFT is not limited to the manner shown in in other words, either the anode 21 or the cathode 23 of the organic light-emitting element is electrically connected to either the source electrode 17 or the drain electrode 16 of the TFT element 18.

Although the display device 1 shown in FIG. 1 is illustrated as if it had a single organic compound layer, the organic compound layer 22 may have a plurality of layers. Furthermore, the cathode 23 is provided thereover with a first protective layer 24 for suppressing the degradation of the organic light-emitting element and a second protective layer 25.

Although the display device 1 shown in FIG. 1 includes transistors as switching elements, metal-insulator-metal (MIM) elements may be used as the switching elements instead of the transistors.

Each transistors of the display device 1 shown in FIG. 1 may be a thin film transistor including an active layer on the insulating surface of the substrate without being limited to a transistor formed in a monocrystalline silicon wafer. The active layer of the thin film transistor may be made of monocrystalline silicon, amorphous silicon, microcrystalline silicon or any other non-rnonocrystalline silicon, or a non-monocrystalline oxide semiconductor, such as indium zinc oxide or indium gallium zinc oxide. A thin film transistor is referred to as a TFT element.

The transistors in the display device 1 shown in FIG. 1 may be formed in the substrate, which may be made of Si. To be formed in the substrate implies that the transistors are formed by working the substrate. In other words, a transistor formed in a substrate implies that the substrate and the transistor are formed in one body.

It depends on the definition of the display device whether the transistors are formed in the substrate. For example, for a display device having a definition of a (SVGA level for 1 inch, it is advantageous to form transistors in a Si substrate.

Figure 3:
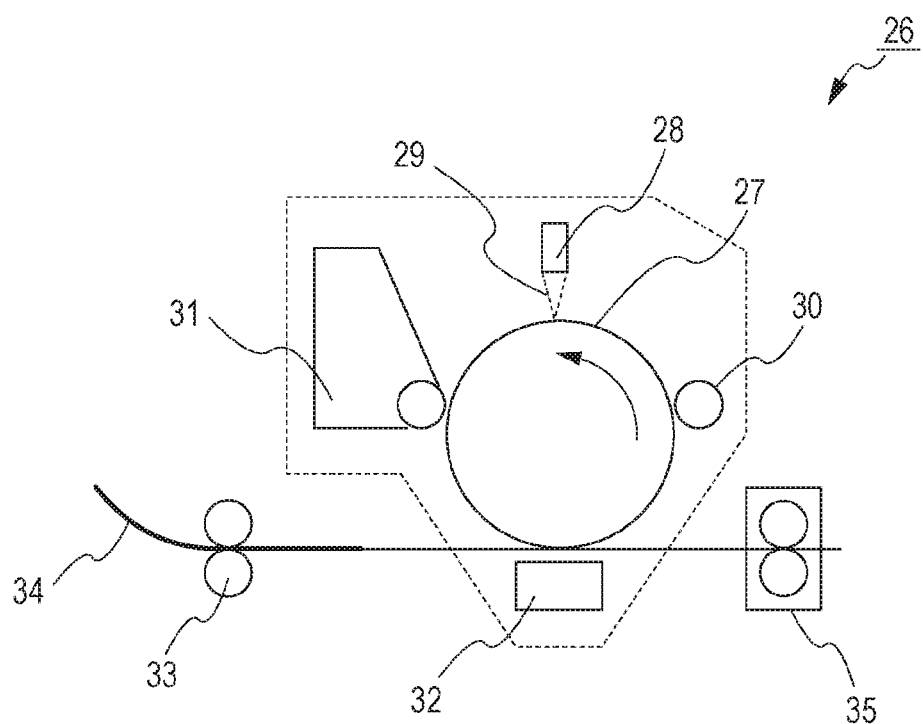
FIG. 3 is a schematic view of an image forming apparatus according to an embodiment of the present invention.

FIG. 3 is a schematic view of an image forming apparatus 26 according to an embodiment of the present invention. The image forming apparatus includes a photosensitive member 27, an exposure light source 28, a developing portion 30, a charging member 31, a transfer device 32, a conveying roller 33, and a fuser 35.

The exposure light source 28 emits light 29 to form an electrostatic latent image on the surface of the photosensitive member 27. The exposure light source 28 includes the organic light-emitting element according to an embodiment of the present invention. The developing portion 30 contains a toner or the like. The charging member 31 charges the photosensitive member 27. The transfer device 32 transfers the developed image to a recording medium 34. The conveying roller 33 conveys the recording medium 34. The recording medium 34 may be a paper sheet. The fuser 35 fixes the image formed on the recording medium.

Figure 4:
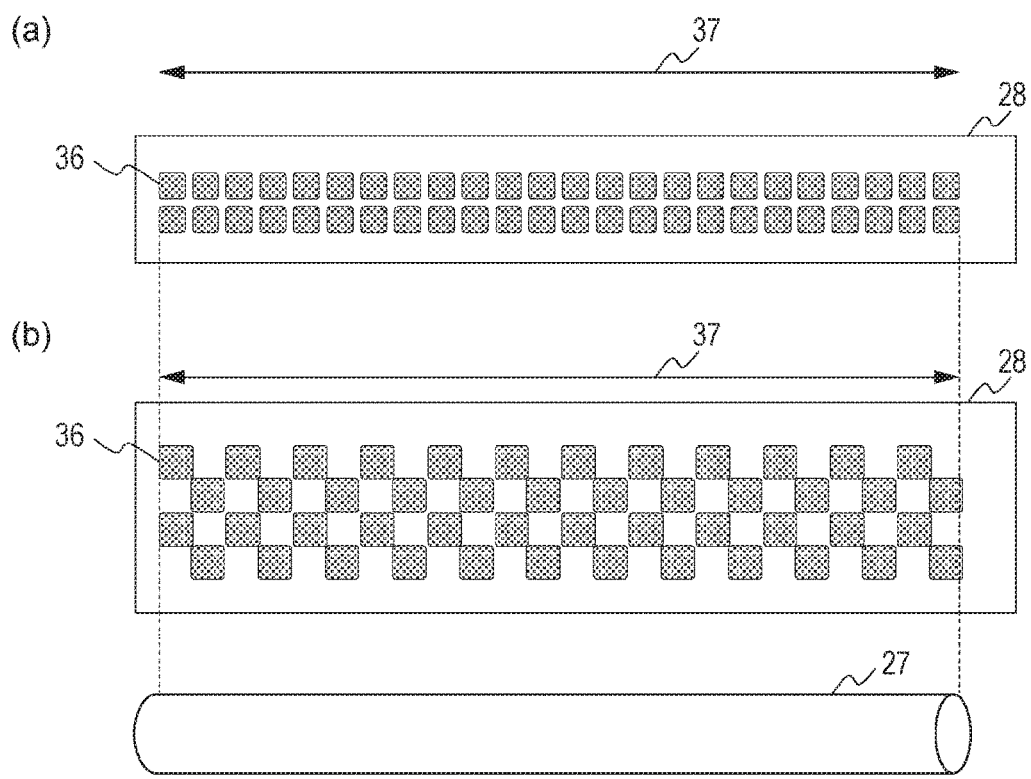
FIG. 4 is a schematic representation of exposure units according to exemplary embodiments of the present invention.

FIG. 4 schematically shows exposure light sources 28 each having emitting portions 36 arranged on a long substrate. In each exposure light source, the organic light-emitting elements are arranged so as to extend in the direction indicated by arrows 37. This direction is the same as the direction of the rotation axis of the photosensitive member 27. This direction can be called the longitudinal direction of the photosensitive member.

Representation (a) shows a form of the exposure light source 28 in which the emitting portions are arranged along the longitudinal direction of the photosensitive member. Representation (b) shows a form different from the form of (a) and in which the emitting portions are arranged alternately in first rows and second rows. The emitting portions in the first rows and the emitting portions in the second rows are arranged at different positions in the column direction.

In each first row, the emitting portions are aligned with spaces therebetween. In each second row, the emitting portions are disposed at positions corresponding to the spaces between each emitting portion in the first row. Thus, the emitting portions are arranged with spaces therebetween in the column direction as well.

In other words, the emitting portions of (b) in FIG. 4 are arranged, for example, in a matrix manner, in a staggered manner, or in a checker.

Figure 5:
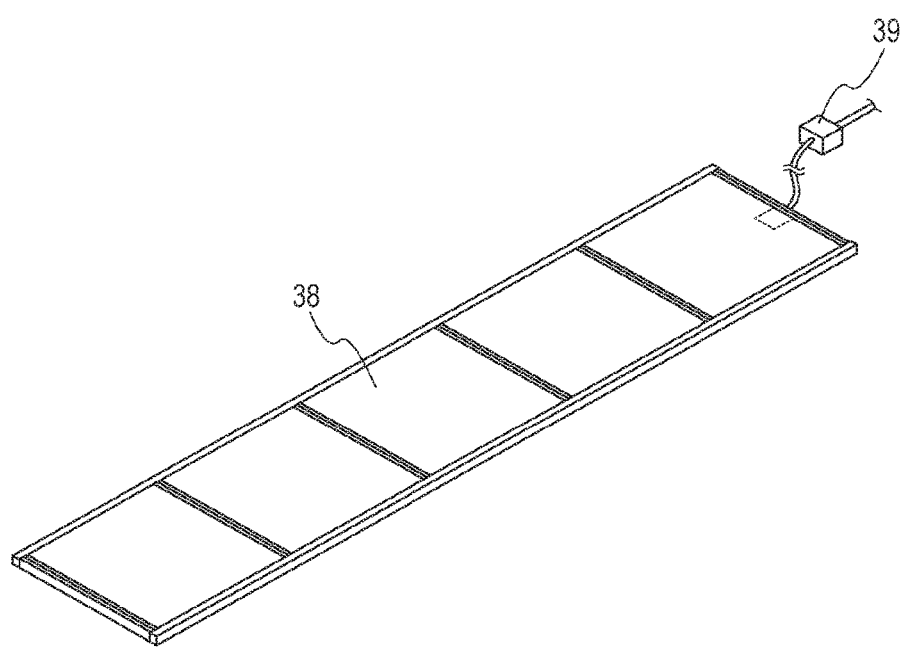
FIG. 5 is a schematic view of a lighting device according to an embodiment of the present invention.

FIG. 5 is a schematic view of a lighting device according to an embodiment of the present invention. The lighting device includes a substrate, organic light-emitting elements 38, and an AC/DC converter circuit 39. In addition, the substrate may be provided with a heat radiation portion (not shown) on the surface thereof opposite the organic light-emitting elements.

As described above, by operating the display device, lighting device or image forming apparatus including the organic light-emitting elements of an embodiment of the present invention, high-quality images can stably be displayed over a long time.

EXAMPLES

Example 1

Synthesis of Exemplified Compound A2

(1) Synthesis of Compound E3

[Chem.18]

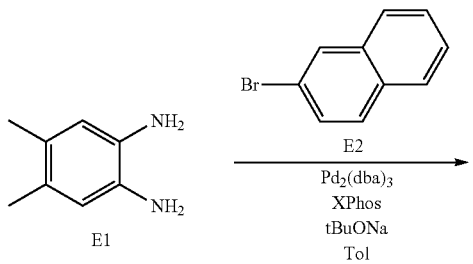

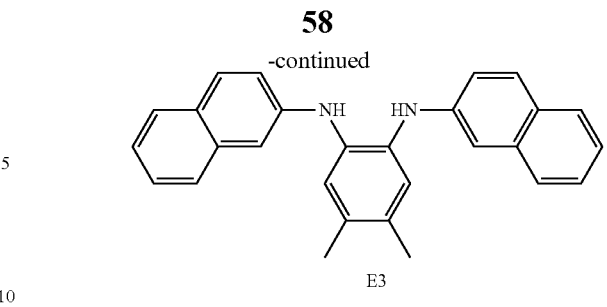

E3

The following compounds and solvent were added to a 100 mF, recovery flask:
E11: 1.36 g (10.0 mmol)
E15: 4.35 g (21.0 mmol)
Tris(dibenzylideneacetone)dipalladium (0): 274 mg (0.3 mmol)
2-Dicyclohexylphosphino-2',4',6'-triisopropylbiphenyl: 333 mg (0.7 mmol)
Sodium tert-butoxide: 2.31 g (24.0 mmol)
Toluene: 50 mL The mixture of these materials was heated to reflux with stirring for 8 hours. After the completion of the reaction, the reaction mixture was filtered through celite and then subjected to separation by adding water. The separated reaction product was purified by silica gel column chromatography (eluent: heptane/chloroform=3/1 to 2/1) to yield 2.53 g of Compound E3 (yield: 65%).

(2) Synthesis of Compound E4

[Chem.19]

The following compound and solvent were added to a 100 mL recovery flask:
E27: 1.94 g (5.00 mmol)
Triethyl orthoformate: 50 mL To the solution of these materials, 0.8 mL of 12 N hydrochloric acid was added, and the mixture was stirred for 5 minutes. Then, 0.05 mL of formic acid was added, and the mixture was heated at 80° C. with stirring for 4 hours. After the completion of the reaction, 20 mL of diethyl ether was added to the cooled reaction mixture. Precipitated crystals were collected by filtration. After being washed with diethyl ether, the crystals were dried at 120° C. under reduced pressure to yield 1.73 g of Compound E28 (yield: 80%).

(3) Synthesis of Exemplified Compound A2

[Chem.20]

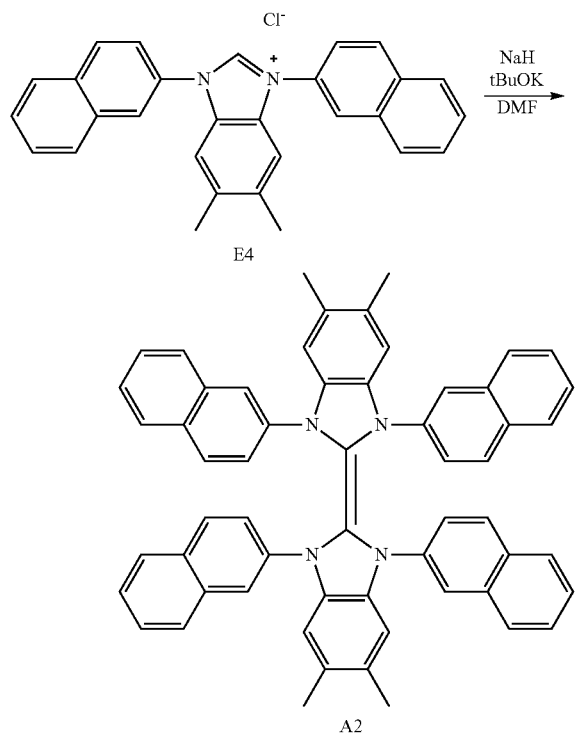

In a nitrogen flow, the following compound and solvent were added to a 100 mL recovery flask:

E4: 435 mg (1.00 mmol)

Dehydrated DMF: 5 mL

After degassing the solution of these materials, 96 mg (4.00 mmol) of sodium hydride was added, followed by stirring for 2 minutes. Then, 44 mg (0.4 mmol) of EBuOK was added, and the sample was heated at 30° C. with stirring for 24 hours. After the completion of the reaction, 10 mL of water degassed with nitrogen was gradually added to the sample with stirring to precipitate the reaction product, and then the solvent was removed using a syringe. After the operation of adding 10 mL of water degassed with nitrogen and then removing the solvent using the syringe was performed twice, 10 mL of degassed hexane was added, and the sample was washed and dispersed with ultrasonic waves. Then, the reaction product was collected by filtration through a membrane filter and washed with hexane to yield 267 mg of yellow powder Exemplified Compound A2 (yield: 67%).

The resulting compound was subjected to matrix-assisted laser desorption/ionization time-of-flight mass spectrometry (MALDI-TOF-MS) using Autoflex LRF manufactured by Bruker.

Measured value: m/z=796.33; Calculated value: 796.36

CV measurement was performed in 0.1 M solution of tetrabutylammonium perchlorate in N,N-dimethylformamide with a Ag/Ag$^+$ reference electrode, a Pt counter electrode and a glassy carbon working electrode. The potential scan rate was 0.5 V/s.

For this measurement, an electrochemical analyzer Model 660C manufactured by ALS was used. Oxidation potential was −0.98 V.

Example 2

Synthesis of Exemplified Compound A4

Exemplified compound A4 was synthesized in the same manner as in operation (1) of Example 1, except that Compound. E5 shown below was used instead of Compound E1.

[Chem. 21]

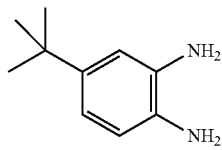

The resulting compound was identified as below.

The resulting compound was subjected to matrix-assisted laser desorption/ionization time-of-flight mass spectrometry (MALDI-TOF-MS) using Autoflex LRF manufactured by Bruker.

Measured value: m/z=852.33; Calculated value: 852.42

The oxidation potential measured with an electrochemical 660C manufactured by ALS was −0.95 V.

Example 3

Synthesis of Exemplified Compound A7

Exemplified compound A7 was synthesized in the same manner as in operation (1) of Example 1, except that Compound E6 shown below was used instead of Compound E1.

[Chem. 22]

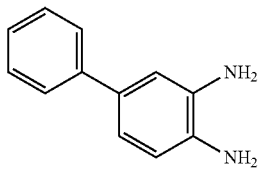

The resulting compound was identified as below.

The resulting compound was subjected to matrix-assisted laser desorption/ionization time-of-flight mass spectrometry (MALDI-TOF-MS) using Autoflex LRF manufactured by Bruker.

Measured value: m/z=892.55; Calculated value: 892.36

The oxidation potential measured with an electrochemical analyzer Model 660C manufactured by ALS was −0.92 V.

Example 4

Synthesis of Exemplified Compound A14

Exemplified compound A14 was synthesized in the same manner as in operation (1) of Example 1, except that Compound E7 shown below was used instead of Compound E2.

[Chem. 23]

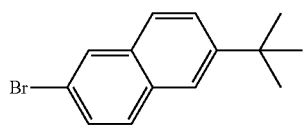

The resulting compound was identified as below.

The resulting compound was subjected to matrix-assisted laser desorption/ionization time-of-flight mass spectrometry (MALDI-TOF-MS) using Autoflex LRF manufactured by Bruker.

Measured value: m/z=1020.77; Calculated value: 1020.61

The oxidation potential measured with an electrochemical analyzer 660C manufactured by ALS was −0.99 V.

Example 5

Synthesis of Exemplified Compound A15

Exemplified compound A15 was synthesized in the same manner as in operation (1) of Example 1, except that Compound E8 shown below was used instead of Compound E2.

[Chem. 24]

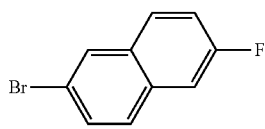

E8

The resulting compound was identified as below.

The resulting compound was subjected to matrix-assisted laser desorption/ionization time-of-flight mass spectrometry (MALDI-TOF-MS) using Autoflex LRF manufactured by Bruker.

Measured value: m/z=812.41; Calculated value: 812.26

The oxidation potential measured with an electrochemical analyzer Model 660C manufactured by ALS was −0.85 V.

Example 6

Synthesis of Exemplified Compound B4

Exemplified compound B4 was synthesized in the same manner as in operation (1) of Example 1, except that Compound E9 shown below was used instead of Compound E1 and Compound E10 shown below was used instead of Compound E2.

[Chem. 25]

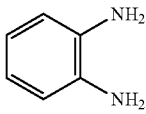

E9

[Chem. 26]

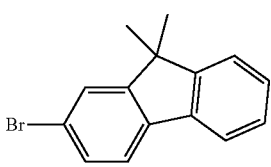

E10

The resulting compound was identified as below.

The resulting compound was subjected to matrix-assisted laser desorption/ionization time-of-flight mass spectrometry (MALDI-TOF-MS) using Autoflex LRF manufactured by Bruker.

Measured value: m/z=1004.86; Calculated value: 1004.48

The oxidation potential measured with an electrochemical analyzer Model 660C manufactured by ALS was −0.98 V, Example 7

Synthesis of Exemplified Compound C2

Exemplified compound C2 was synthesized in the same manner as in operation (1) of Example 1, except that Compound E11 shown below was used instead of Compound E2.

[Chem. 27]

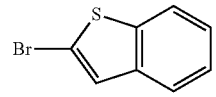

E11

The resulting compound was identified as below.

The resulting compound was subjected to matrix-assisted laser desorption/ionization time-of-flight mass spectrometry (MALDI-TOF-MS) using Autoflex LRF manufactured by Bruker.

Measured value: m/z=820.33; Calculated value: 820.18

The oxidation potential measured with an electrochemical analyzer Model 660C manufactured by ALS was −0.74 V.

Example 8

Synthesis of Exemplified Compound C12

Exemplified compound C12 was synthesized in the same manner as in operation (1) of Example 1, except that Compound E12 shown below was used instead of Compound E2.

[Chem. 28]

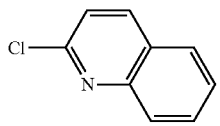

E12

The resulting compound was identified as below.

The resulting compound was subjected to matrix-assisted laser desorption/ionization time-of-flight mass spectrometry (MALDI-TOF-MS) using Autoflex LRF manufactured by Bruker.

Measured value: m/z=800.65; Calculated value: 800.34

The oxidation potential measured with an electrochemical analyzer Model 660C manufactured by ALS was −0.73 V, Example 9

An organic light-emitting element was produced by forming an anode, a hole transport layer, an electron blocking layer, a luminescent layer, a hole blocking layer, an electron transport layer and a cathode in that order on a substrate.

First, an ITO layer was formed on a glass substrate and then patterned into an ITO electrode (anode). The thickness of the ITO electrode was 100 nm at that time. The resulting substrate having the ITO electrode thereon was used as an ITO substrate in the subsequent step.

Organic compound layers and an electrode layer, shown in Table 2, were continuously formed on the ITO substrate. At this time, the opposing electrode (metal electrode layer or cathode) was formed with an area of 3 mm².

TABLE 2

| | Material | Thickness (nm) |
|---|---|---|
| Hole transport layer | G-1 | 30 |
| Electron blocking layer | G-2 | 10 |
| Luminescent layer | G-3 (Host) | 30 |
| | G-4 (Guest) | |
| | (G-3:G-4 = 98:2 (weight ratio)) | |
| Hole blocking layer | G-5 | 10 |
| Electron transport layer | G-6 | 15 |

TABLE 2-continued

| | Material | Thickness (nm) |
|---|---|---|
| Electron injection layer | G-7<br>G-8<br>(G-7:G-8 = 50:50 (weight ratio)) | 15 |
| Metal electrode layer | Al | 100 |

Before forming the metal electrode layer, the sample was allowed to stand in the air for 10 minutes and then the metal electrode layer was formed.

As Compounds G1 to G8 were used 2,2'-bibenzo[d]imidazolidene compounds having condensed rings at the 1-, 1'-, 3- and 3'-positions and Comparative Compounds (3) and (4) shown in Table 3.

TABLE 3

| | G1 | G2 | G3 | G4 | G5 | G6 | G7 | G8 | Light Emission |
|---|---|---|---|---|---|---|---|---|---|
| Example 1 | HT1 | HT7 | EM13 | RD1 | ET2 | ET2 | EI6 | A1 | Good |
| Example 2 | HT1 | HT7 | EM13 | RD1 | ET2 | ET2 | EI6 | A5 | Good |
| Example 3 | HT1 | HT7 | EM13 | RD1 | ET2 | ET2 | EI6 | B4 | Good |
| Example 4 | HT1 | HT7 | EM13 | RD1 | ET2 | ET2 | EI6 | C2 | Good |
| Comparative Example 1 | HT1 | HT7 | EM13 | RD1 | ET2 | ET2 | EI6 | Comparative compound 3 | Bad |
| Comparative Example 2 | HT1 | HT7 | EM13 | RD1 | ET2 | ET2 | EI6 | Comparative compound 4 | Bad |

Light emission from each element was examined at a voltage of 8 V. As a result, the elements using the present organic compound emitted light, but the elements using Comparative Compound (3) or (4) did not emit light.

This is probably because the Comparative Compounds deteriorated when the element was exposed to the air, thus losing the electron injectability thereof.

Examples 5-10

An organic light-emitting element was produced by forming an anode, a hole transport layer, an electron blocking layer, a luminescent layer, a hole blocking layer, an electron transport layer and a cathode in that order on a substrate.

First, an ITO layer was formed on a glass substrate and then patterned into an ITO electrode (anode). The thickness of the ITO electrode was 100 nm at that time. The resulting substrate having the ITO electrode thereon was used as an ITO substrate in the subsequent step.

Organic compound layers and an electrode layer, shown in Table 4, were continuously formed on the ITO substrate. At this time, the opposing electrode (metal electrode layer or cathode) was formed with an area of 3 mm².

TABLE 4

| | Material | Thickness (nm) |
|---|---|---|
| Hole transport layer | G-1 | 30 |
| Electron blocking layer | G-2 | 10 |
| Luminescent layer | G-3 (Host)<br>G-4 (Guest)<br>(G-3:G-4 = 98:2 (weight ratio)) = 98:2 (weight ratio)) | 30 |
| Hole blocking layer | G-5 | 10 |
| Electron transport layer | G-6 | 15 |
| Electron injection layer | G-7<br>G-8<br>(G-7:G-8 = 50:50 (weight ratio)) | 15 |
| Metal electrode layer | G-9 | 100 |

As Compounds G1 to G8 were used 1,1',3,3'-tetrahydro-2,2'-bibenzo[d]imidazolidene compounds having condensed rings at the 1-, 1'-, 3- and 3'-positions shown in Table 5.

TABLE 5

|  | G1 | G2 | G3 | G4 | G5 | G6 | G8 | G9 | Emission efficiency (cd/A) | Voltage (V) |
|---|---|---|---|---|---|---|---|---|---|---|
| Example 5 | HT2 | HT7 | EM12 | RD1 | ET10 | EI6 | A3 | Ag | 4 | 5 |
| Example 6 | HT2 | HT8 | EM3 | BD4 | ET4 | EI14 | A5 | Ag | 6 | 6 |
| Example 7 | HT6 | HT8 | EM4 | GD4 | EM6 | EI6 | B14 | Au | 22 | 6 |
| Example 8 | HT6 | HT7 | EM8 | RD4 | ET6 | EI7 | B7 | Ag:Mg = 1:1 | 8 | 6 |
| Example 9 | HT2 | HT7 | EM14 | RD2 | ET9 | EI8 | C5 | Ag | 4 | 5 |
| Example 10 | HT2 | HT7 | EM4 | BD7 | EI9 | EI9 | C12 | Ag:Cu = 5.1 | 6 | 5 |

Examples 11-15

An organic light-emitting element was produced by forming an anode, a hole transport layer, an electron blocking layer, a luminescent layer, a hole blocking layer, an electron transport layer and a cathode in that order on a substrate.

First, an ITO layer was formed on a glass substrate and then patterned into an ITO electrode (anode). The thickness of the ITO electrode was 100 nm at that time. The resulting substrate having the ITO electrode thereon was used as an ITO substrate in the subsequent step.

Organic compound layers and an electrode layer, shown in Table 6, were continuously formed on the ITO substrate. At this time, the opposing electrode (metal electrode layer or cathode) was formed with an area of 3 mm$^2$.

TABLE 6

|  | Material | Thickness (nm) |
|---|---|---|
| Hole transport layer | G-1 | 30 |
| Electron blocking layer | G-2 | 10 |
| Luminescent layer | G-3 (Host) | 30 |
|  | G-4 (Guest) |  |
|  | (G-3:G-4 = 98:2 (weight ratio)) |  |
| Hole blocking layer | G-5 | 10 |
| Electron transport layer | G-6 | 26 |
| Electron injection layer | G-8 | 4 |
| Metal electrode layer | G-9 | 100 |

As Compounds G1 to G6 and G8 were used the compounds as shown Table 7. Also, metals shown in Table 7 were used as G9. If metals were mixed, the proportions thereof were shown on a weight basis. Compound G8 was any one of the 2,2'-benzo[d]imidazolidene compounds having condensed rings at the 1-, 1'-, 3- and 3'-positions.

TABLE 7

|  | G1 | G2 | G3 | G4 | G5 | G6 | G8 | G9 | Emission efficiency (cd/A) | Voltage (V) |
|---|---|---|---|---|---|---|---|---|---|---|
| Example 11 | HT6 | HT7 | EM13 | RD1 | EI6 | EI6 | A2 | Ag:Mg = 1:1 | 4 | 4 |
| Example 12 | HT6 | HT7 | EM4 | BD6 | EI9 | EI9 | A4 | Ag | 6 | 5 |
| Example 13 | HT2 | HT8 | EM7 | GD6 | EI4 | EI17 | A7 | Au | 25 | 6 |
| Example 14 | HT2 | HT8 | EM14 | RD1 | EI14 | EI14 | B5 | Ag:Al = 1:1 | 4 | 5 |
| Example 15 | HT1 | HT7 | EM8 | BD8 | EI4 | EI12 | C13 | Al | 5 | 6 |

As described above with reference to the Examples, by using a 2,2'-benzo[d]imidazolidene compound having condensed rings at the 1-, 1'-, 3- and 3'-positions according to an embodiment of the present invention in the electron injection layer of an organic light-emitting element, the organic light-emitting element can be stable in the air. Thus, the organic light-emitting element can be stable and have a long life.

As described above with reference to the Examples, also, by using a 2,2'-benzo[d]imidazolidene compound having condensed rings at the 1-, 1'-, 3- and 3'-positions according to an embodiment of the present invention in the electron injection layer, the organic light-emitting element can be stable to water and humidity. Thus, the organic light-emitting element can exhibit a high emission efficiency and a long life.

According to an embodiment of the present invention, there is provided a 2,2'-benzo[d]imidazolidene compound having condensed rings at the 1-, 1'-, 3- and 3'-positions that is stable to oxidation in the air.

While the present invention has been described with reference to exemplary embodiments, it is to be understood that the invention. is not limited to the disclosed exemplary embodiments. The scope of the following claims is to be accorded the broadest interpretation so as to encompass all such modifications and equivalent structures and functions.

The invention claimed is:

1. A 2,2'-benzo[d]imidazolidene compound expressed by the following general formula (1):

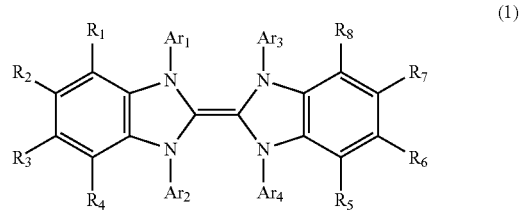

wherein $Ar_1$ to $Ar_4$ each represent a substituted or unsubstituted condensed ring, and $R_1$ to $R_8$ each represent a hydro- gen atom or a substituent selected from the group consisting of halogen atoms, alkyl groups having a carbon number in the range of 1 to 8, and substituted or unsubstituted aromatic hydrocarbon groups.

2. The 2,2'-benzo[d]imidazolidene compound according to claim 1, wherein the atom of each of the condensed rings, adjacent to the atom bound to the nitrogen atom of the 1,1',3,3'-tetrahydro-2,2'-ibenzo[d]imidazolidene skeleton in general formula (1) has a hydrogen atom.

3. The 2,2'-benzo[d]imidazolidene compound according to claim 1, wherein $Ar_1$ and $Ar_2$ are the same substituent, and $Ar_3$ and $Ar_4$ are the same substituent.

4. An organic electronic element comprising:
a pair of electrodes; and an organic compound layer between the pair of electrodes, the organic compound layer containing the 2,2'-bibenzo[d]imidazolidene compound as set forth in claim 1.

5. An organic light-emitting element comprising:
an anode;
a cathode;
a luminescent layer between the anode and the cathode; and
an organic compound layer between the cathode and the luminescent layer, the organic compound layer containing the 2,2'-bibenzo[d]imidazolidene compound as set forth in claim 1.

6. The organic light-emitting element according to claim 5, wherein the organic compound layer contains an additional organic compound different from the 2,2'-bibenzo[d]imidazolidene compound.

7. The organic light-emitting element according to claim 6, wherein the additional organic compound has a higher oxidation potential than the 2,2'-bibenzo[d]imidazolidene compound.

8. The organic light-emitting element according to claim 6, wherein the content of the additional organic compound in the organic compound layer is in the range of more than 0% by weight to 80% by weight relative to the total weight of the organic compound layer.

9. The organic light-emitting element according to claim 5, wherein the organic compound layer is in contact with the cathode.

10. A display device comprising:
a plurality of emission points, each including the organic light-emitting element as set forth in claim 5, and
an active element connected to the organic light-emitting element.

11. The display device according to claim 10, wherein the active element is a transistor containing an oxide semiconductor in an active region thereof.

12. An image information processing apparatus comprising:
a display portion capable of displaying an image, the display portion being the display device as set forth in claim 10;
an input portion into which image information is input; and
a processing portion capable of processing the image information.

13. A lighting device comprising:
the organic light-emitting element as set forth in claim 5; and
an AC/DC converter connected to the organic light-emitting element.

14. A lighting device comprising:
a substrate;
a heat radiation portion capable of dissipating heat from the lighting device; and
the organic light-emitting element as set forth in claim 5.

15. An image forming apparatus comprising:
a photosensitive member;
an exposure portion capable of exposing the photosensitive member, the exposure portion including the organic light-emitting element as set forth in claim 5;
a charging member capable of charging the photosensitive member; and
a developing portion capable of applying a developer to the photosensitive member.

16. An exposure unit capable of exposing a photosensitive member, the exposure unit comprising:
a plurality of organic light-emitting elements as set forth in claim 5, the light-emitting elements being arranged in a line along the longitudinal direction of the photosensitive member.

* * * * *